(12) United States Patent
Wales et al.

(10) Patent No.: US 10,179,012 B2
(45) Date of Patent: *Jan. 15, 2019

(54) SYSTEMS AND METHODS FOR ORTHOPEDIC REPAIR

(71) Applicant: CARTIVA, INC., Alpharetta, GA (US)

(72) Inventors: Lawrence W. Wales, Maplewood, MN (US); Jeff Peters, Excelsior, MN (US)

(73) Assignee: Cartiva, Inc., Alpharetta, GA (US)

( * ) Notice: Subject to any disclaimer, the term of this patent is extended or adjusted under 35 U.S.C. 154(b) by 537 days.

This patent is subject to a terminal disclaimer.

(21) Appl. No.: 14/763,502

(22) PCT Filed: Jan. 27, 2014

(86) PCT No.: PCT/US2014/013242
§ 371 (c)(1),
(2) Date: Jul. 24, 2015

(87) PCT Pub. No.: WO2014/117107
PCT Pub. Date: Jul. 31, 2014

(65) Prior Publication Data
US 2015/0351815 A1    Dec. 10, 2015

Related U.S. Application Data

(60) Provisional application No. 61/757,553, filed on Jan. 28, 2013, provisional application No. 61/914,341, filed on Dec. 10, 2013.

(51) Int. Cl.
*A61B 17/72* (2006.01)
*A61B 17/84* (2006.01)
(Continued)

(52) U.S. Cl.
CPC ...... *A61B 17/7225* (2013.01); *A61B 17/0401* (2013.01); *A61B 17/7266* (2013.01);
(Continued)

(58) Field of Classification Search
CPC ...... A61B 17/04; A61B 17/0401; A61B 17/72; A61B 17/7216; A61B 17/7225;
(Continued)

(56) References Cited

U.S. PATENT DOCUMENTS 3,131,957 A    5/1964  Musto
3,648,705 A    3/1972  Lary
(Continued)

FOREIGN PATENT DOCUMENTS

DE    43239595    7/1994
EP    0020021     12/1980
(Continued)

OTHER PUBLICATIONS

Int'l Search Report and Written Opinion in Int'l App No. PCT/US14/13242, dated Jun. 23, 2014 (19 pgs).
(Continued)

*Primary Examiner* — Eric S Gibson
(74) *Attorney, Agent, or Firm* — Knobbe, Martens, Olson & Bear, LLP

(57) ABSTRACT

According to some embodiments, an implant for correcting a deformity in or near a joint of a subject includes an implant body having an internal lumen, a suture side hole or window extending through a wall of the implant body and providing access to the internal lumen through an exterior of the implant body, a tension assembly comprising a first bone anchor and a second bone anchor, wherein the first and second bone anchors are configured to be placed on opposite sides of the implant body, and an adjustable suture loop coupling the first bone anchor to the second bone anchor, wherein at least a portion of the at least one adjustable suture loop is positioned within the internal lumen of the implant body.

17 Claims, 21 Drawing Sheets

(51) Int. Cl.
   *A61F 2/08* (2006.01)
   *A61B 17/88* (2006.01)
   *A61B 17/04* (2006.01)
   *A61B 17/06* (2006.01)

(52) U.S. Cl.
   CPC ........ *A61B 17/7291* (2013.01); *A61B 17/844* (2013.01); *A61B 17/8869* (2013.01); *A61F 2/08* (2013.01); *A61F 2/0811* (2013.01); *A61B 2017/0412* (2013.01); *A61B 2017/0414* (2013.01); *A61B 2017/0417* (2013.01); *A61B 2017/0424* (2013.01); *A61B 2017/0427* (2013.01); *A61B 2017/0432* (2013.01); *A61B 2017/0446* (2013.01); *A61B 2017/0458* (2013.01); *A61B 2017/0475* (2013.01); *A61B 2017/0496* (2013.01); *A61B 2017/06185* (2013.01); *A61F 2002/0829* (2013.01); *A61F 2002/0852* (2013.01); *A61F 2002/0888* (2013.01); *A61F 2250/0007* (2013.01)

(58) Field of Classification Search
   CPC ............ A61B 17/7233; A61B 17/7258; A61B 17/7283; A61B 17/7291; A61B 2017/0412; A61B 2017/0414; A61B 2017/0427; A61B 2017/0429; A61B 2017/0435; A61B 2017/0437; A61B 2017/0445; A61B 2017/0464
   USPC .......................................... 606/232, 300–321
   See application file for complete search history.

(56) References Cited

U.S. PATENT DOCUMENTS

| | | |
|---|---|---|
| 3,752,516 A | 8/1973 | Mumma |
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Field |
| 4,059,115 A | 11/1977 | Jamushev |
| 4,224,413 A | 9/1980 | Burbidge |
| 4,235,238 A | 11/1980 | Ogiu et al. |
| 4,262,665 A | 4/1981 | Roalstad et al. |
| 4,502,161 A | 3/1985 | Wall |
| 4,512,338 A | 4/1985 | Balko et al. |
| 4,532,926 A | 8/1985 | O'Holla |
| 4,545,374 A | 10/1985 | Jacobson |
| 4,602,635 A | 7/1986 | Mulhollan et al. |
| 4,632,100 A | 12/1986 | Somers et al. |
| 4,662,886 A | 5/1987 | Moorse |
| 4,663,358 A | 5/1987 | Hyon et al. |
| 4,669,473 A | 6/1987 | Richards et al. |
| 4,678,459 A | 7/1987 | Onik et al. |
| 4,731,084 A | 3/1988 | Dunn et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,790,850 A | 12/1988 | Dunn et al. |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,863,477 A | 9/1989 | Monson |
| 4,873,976 A | 10/1989 | Schreiber |
| 4,884,572 A | 12/1989 | Bays et al. |
| 4,890,612 A | 1/1990 | Kensey |
| 4,895,148 A | 1/1990 | Bays et al. |
| 4,898,156 A | 2/1990 | Gatturna |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,377 A | 8/1990 | Kovach |
| 4,946,378 A | 8/1990 | Hirayama et al. |
| 4,955,908 A | 9/1990 | Frey et al. |
| 4,959,069 A | 9/1990 | Brennan et al. |
| 4,976,715 A | 12/1990 | Bays et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kushlich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,682 A | 1/1993 | Chow |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,203,787 A | 4/1993 | Noblitt et al. |
| 5,204,106 A | 4/1993 | Schepers et al. |
| 5,207,695 A | 5/1993 | Trout |
| 5,211,650 A | 5/1993 | Noda |
| 5,222,962 A | 6/1993 | Burkhart |
| 5,222,974 A | 6/1993 | Kensey et al. |
| 5,224,946 A | 7/1993 | Hayhurst et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,269,809 A | 12/1993 | Hayhurst et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,318,575 A | 6/1994 | Chesterfield et al. |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,662 A | 12/1994 | Stone et al. |
| 5,370,697 A | 12/1994 | Baumgartner |
| 5,374,268 A | 12/1994 | Sander |

(56) References Cited

U.S. PATENT DOCUMENTS

| | | |
|---|---|---|
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,359 A | 4/1995 | Pierce |
| 5,405,360 A | 4/1995 | Tovey |
| 5,411,523 A | 5/1995 | Goble |
| 5,417,691 A | 5/1995 | Hayhurst |
| 5,417,699 A | 5/1995 | Klein et al. |
| 5,417,712 A | 5/1995 | Whittaker et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,439,464 A | 8/1995 | Shapiro |
| 5,441,502 A | 8/1995 | Bartlett |
| 5,456,720 A | 10/1995 | Schultz et al. |
| 5,464,407 A | 11/1995 | McGuire |
| 5,464,425 A | 11/1995 | Skiba |
| 5,464,426 A | 11/1995 | Bonutti |
| 5,464,427 A | 11/1995 | Curtis et al. |
| 5,470,337 A | 11/1995 | Moss |
| 5,489,307 A | 2/1996 | Kuslich et al. |
| 5,492,697 A | 2/1996 | Boyan et al. |
| 5,496,348 A | 3/1996 | Bonutti |
| 5,500,000 A | 3/1996 | Feagin et al. |
| 5,507,754 A | 4/1996 | Green et al. |
| 5,507,755 A | 4/1996 | Gresl et al. |
| 5,514,180 A | 5/1996 | Heggeness et al. |
| 5,520,696 A | 5/1996 | Wenstrom, Jr. |
| 5,520,700 A | 5/1996 | Beyar et al. |
| 5,527,342 A | 6/1996 | Pietrzak et al. |
| 5,527,343 A | 6/1996 | Bonutti |
| 5,529,075 A | 6/1996 | Clark |
| 5,531,678 A | 7/1996 | Tomba et al. |
| 5,531,759 A | 7/1996 | Kensey et al. |
| 5,534,012 A | 7/1996 | Bonutti |
| 5,534,028 A | 7/1996 | Bao et al. |
| 5,534,030 A | 7/1996 | Navarro et al. |
| 5,540,703 A | 7/1996 | Barker et al. |
| 5,540,704 A | 7/1996 | Gordon et al. |
| 5,540,715 A | 7/1996 | Katsaros et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |
| 5,556,429 A | 9/1996 | Felt |
| 5,562,684 A | 10/1996 | Kammerer |
| 5,562,689 A | 10/1996 | Green et al. |
| 5,562,736 A | 10/1996 | Ray et al. |
| 5,562,738 A | 10/1996 | Boyd et al. |
| 5,569,242 A | 10/1996 | Lax et al. |
| 5,569,252 A | 10/1996 | Justin et al. |
| 5,569,303 A | 10/1996 | Johnson |
| 5,569,306 A | 10/1996 | Thal |
| 5,571,189 A | 11/1996 | Kuslich |
| 5,573,286 A | 11/1996 | Rogozinski |
| 5,573,548 A | 11/1996 | Nazre et al. |
| 5,578,057 A | 11/1996 | Wenstrom, Jr. |
| 5,582,616 A | 12/1996 | Bolduc et al. |
| 5,584,862 A | 12/1996 | Bonutti |
| 5,591,177 A | 1/1997 | Lehrer |
| 5,591,223 A | 1/1997 | Lock et al. |
| 5,593,425 A | 1/1997 | Bonutti et al. |
| 5,599,279 A | 2/1997 | Slotman et al. |
| 5,601,557 A | 2/1997 | Hayhurst |
| 5,601,571 A | 2/1997 | Moss |
| 5,613,974 A | 3/1997 | Andreas et al. |
| 5,618,314 A | 4/1997 | Harwin et al. |
| 5,620,012 A | 4/1997 | Benderev et al. |
| 5,624,463 A | 4/1997 | Stone et al. |
| 5,626,612 A | 5/1997 | Bartlett et al. |
| 5,626,613 A | 5/1997 | Schmieding |
| 5,626,614 A | 5/1997 | Hart |
| 5,628,756 A | 5/1997 | Barker et al. |
| 5,634,931 A | 6/1997 | Kugel |
| 5,634,944 A | 6/1997 | Magram |
| 5,643,319 A | 7/1997 | Green et al. |
| 5,643,320 A | 7/1997 | Lower et al. |
| 5,645,084 A | 7/1997 | McKay |
| 5,645,597 A | 7/1997 | Krapiva |
| 5,647,874 A | 7/1997 | Hayhurst |
| 5,649,945 A | 7/1997 | Ray et al. |
| 5,658,343 A | 8/1997 | Hauselmann et al. |
| 5,662,658 A | 9/1997 | Wenstrom, Jr. |
| 5,662,681 A | 9/1997 | Nash et al. |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,417 A | 11/1997 | Cooper |
| 5,683,418 A | 11/1997 | Luscombe et al. |
| 5,683,419 A | 11/1997 | Thal |
| 5,683,465 A | 11/1997 | Shinn et al. |
| 5,690,677 A | 11/1997 | Schmieding et al. |
| 5,695,525 A | 12/1997 | Mulhauser et al. |
| 5,697,950 A | 12/1997 | Fucci et al. |
| 5,699,657 A | 12/1997 | Paulson |
| 5,702,449 A | 12/1997 | McKay |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,704,943 A | 1/1998 | Yoon et al. |
| 5,709,708 A | 1/1998 | Thal |
| 5,716,404 A | 2/1998 | Vacanti et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,718,717 A | 2/1998 | Bonutti |
| 5,725,552 A | 3/1998 | Kotula et al. |
| 5,725,577 A | 3/1998 | Saxon |
| 5,728,109 A | 3/1998 | Schulze et al. |
| 5,728,150 A | 3/1998 | McDonald et al. |
| 5,730,744 A | 3/1998 | Justin et al. |
| 5,733,307 A | 3/1998 | Dinsdale |
| 5,733,337 A | 3/1998 | Carr, Jr. et al. |
| 5,735,875 A | 4/1998 | Bonutti |
| 5,736,746 A | 4/1998 | Furutoh |
| 5,743,917 A | 4/1998 | Saxon |
| 5,746,755 A | 5/1998 | Wood et al. |
| 5,752,964 A | 5/1998 | Mericle |
| 5,755,797 A | 5/1998 | Baumgartner |
| 5,759,189 A | 6/1998 | Ferragamo et al. |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,782,860 A | 7/1998 | Epstein et al. |
| 5,782,864 A | 7/1998 | Lizardi |
| 5,785,705 A | 7/1998 | Baker |
| 5,786,217 A | 7/1998 | Tubo et al. |
| 5,788,625 A | 8/1998 | Plouhar et al. |
| 5,792,152 A | 8/1998 | Klein et al. |
| 5,797,929 A | 8/1998 | Andreas et al. |
| 5,800,549 A | 9/1998 | Bao et al. |
| 5,800,550 A | 9/1998 | Sertich |
| 5,810,848 A | 9/1998 | Hayhurst |

(56) References Cited

U.S. PATENT DOCUMENTS

| | | |
|---|---|---|
| 5,810,851 A | 9/1998 | Yoon |
| 5,814,051 A | 9/1998 | Wenstrom, Jr. |
| 5,823,994 A | 10/1998 | Sharkey et al. |
| 5,824,008 A | 10/1998 | Bolduc et al. |
| 5,824,011 A | 10/1998 | Stone et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,827,325 A | 10/1998 | Landgrebe et al. |
| 5,827,328 A | 10/1998 | Butterman |
| 5,836,315 A | 11/1998 | Benderev et al. |
| 5,842,477 A | 12/1998 | Naughton et al. |
| 5,843,084 A | 12/1998 | Hart et al. |
| 5,846,261 A | 12/1998 | Kotula et al. |
| 5,849,331 A | 12/1998 | Ducheyne et al. |
| 5,851,219 A | 12/1998 | Goble et al. |
| 5,853,422 A | 12/1998 | Huebsch et al. |
| 5,855,614 A | 1/1999 | Stevens et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,868,762 A | 2/1999 | Cragg et al. |
| 5,879,366 A | 3/1999 | Shaw et al. |
| 5,888,220 A | 3/1999 | Felt et al. |
| 5,888,222 A | 3/1999 | Coates |
| 5,888,226 A | 3/1999 | Rogozinski |
| 5,891,146 A | 4/1999 | Simon et al. |
| 5,893,592 A | 4/1999 | Schulze et al. |
| 5,893,889 A | 4/1999 | Harrington |
| 5,895,426 A | 4/1999 | Scarborough et al. |
| 5,899,920 A | 5/1999 | DeSatnick et al. |
| 5,904,703 A | 5/1999 | Gilson |
| 5,916,225 A | 6/1999 | Kugel |
| 5,919,235 A | 7/1999 | Husson et al. |
| 5,922,026 A | 7/1999 | Chin |
| 5,922,028 A | 7/1999 | Plouhar et al. |
| 5,928,284 A | 7/1999 | Mehdizadeh |
| 5,935,147 A | 8/1999 | Kensey et al. |
| 5,941,439 A | 8/1999 | Kammerer et al. |
| 5,944,738 A | 8/1999 | Amplatz et al. |
| 5,948,001 A | 9/1999 | Larsen |
| 5,948,002 A | 9/1999 | Bonutti |
| 5,954,716 A | 9/1999 | Sharkey et al. |
| 5,954,767 A | 9/1999 | Pajotin et al. |
| 5,957,939 A | 9/1999 | Heaven et al. |
| 5,957,953 A | 9/1999 | DiPoto et al. |
| 5,961,538 A | 10/1999 | Pedlick et al. |
| 5,964,783 A | 10/1999 | Grafton et al. |
| 5,964,807 A | 10/1999 | Gan et al. |
| 5,970,697 A | 10/1999 | Jacobs et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 5,980,558 A | 11/1999 | Wiley |
| 5,981,826 A | 11/1999 | Ku et al. |
| 5,984,948 A | 11/1999 | Hasson |
| 6,001,130 A | 12/1999 | Bryan et al. |
| 6,007,567 A | 12/1999 | Bonutti |
| 6,007,570 A | 12/1999 | Sharkey et al. |
| 6,007,575 A | 12/1999 | Samuels |
| 6,010,525 A | 1/2000 | Bonutti et al. |
| 6,019,792 A | 2/2000 | Cauthen |
| 6,019,793 A | 2/2000 | Perren et al. |
| 6,024,096 A | 2/2000 | Buckberg |
| 6,024,754 A | 2/2000 | Engelson |
| 6,024,758 A | 2/2000 | Thal |
| 6,027,523 A | 2/2000 | Schmieding |
| 6,027,527 A | 2/2000 | Asano et al. |
| 6,036,699 A | 3/2000 | Andreas et al. |
| 6,039,761 A | 3/2000 | Li et al. |
| 6,039,762 A | 3/2000 | McKay |
| 6,045,561 A | 4/2000 | Marshall et al. |
| 6,045,573 A | 4/2000 | Wenstrom, Jr. et al. |
| 6,053,909 A | 4/2000 | Shadduck |
| 6,063,378 A | 5/2000 | Nohara et al. |
| 6,066,146 A | 5/2000 | Carroll et al. |
| 6,066,776 A | 5/2000 | Goodwin et al. |
| 6,068,648 A | 5/2000 | Cole et al. |
| 6,073,051 A | 6/2000 | Sharkey et al. |
| 6,080,182 A | 6/2000 | Shaw et al. |
| 6,093,205 A | 7/2000 | McLeod et al. |
| 6,095,149 A | 8/2000 | Sharkey et al. |
| 6,099,514 A | 8/2000 | Sharkey et al. |
| 6,102,934 A | 8/2000 | Li |
| 6,106,545 A | 8/2000 | Egan |
| 6,113,609 A | 9/2000 | Adams |
| 6,113,623 A | 9/2000 | Sgro |
| 6,113,639 A | 9/2000 | Ray et al. |
| 6,117,162 A | 9/2000 | Schmieding et al. |
| 6,123,715 A | 9/2000 | Amplatz |
| 6,126,682 A | 10/2000 | Sharkey et al. |
| 6,139,565 A | 10/2000 | Stone et al. |
| 6,140,452 A | 10/2000 | Felt et al. |
| 6,143,006 A | 11/2000 | Chan et al. |
| 6,143,017 A | 11/2000 | Thal |
| 6,146,380 A | 11/2000 | Racz et al. |
| 6,146,406 A | 11/2000 | Shluzas et al. |
| 6,146,422 A | 11/2000 | Lawson |
| 6,162,203 A | 12/2000 | Haago |
| 6,168,598 B1 | 1/2001 | Martello |
| 6,171,317 B1 | 1/2001 | Jackson et al. |
| 6,171,318 B1 | 1/2001 | Kugel et al. |
| 6,171,329 B1 | 1/2001 | Shaw et al. |
| 6,174,322 B1 | 1/2001 | Schneidt |
| 6,176,863 B1 | 1/2001 | Kugel et al. |
| 6,179,874 B1 | 1/2001 | Cauthen |
| 6,179,879 B1 | 1/2001 | Robinson et al. |
| 6,183,518 B1 | 2/2001 | Tormala et al. |
| 6,187,048 B1 | 2/2001 | Milner et al. |
| 6,190,401 B1 | 2/2001 | Green et al. |
| 6,200,329 B1 | 3/2001 | Fung et al. |
| 6,203,554 B1 | 3/2001 | Roberts |
| 6,203,565 B1 | 3/2001 | Bonutti |
| 6,206,895 B1 | 3/2001 | Levinson |
| 6,206,921 B1 | 3/2001 | Guagliano et al. |
| 6,221,092 B1 | 4/2001 | Koike et al. |
| 6,221,109 B1 | 4/2001 | Geistlich et al. |
| 6,224,630 B1 | 5/2001 | Bao et al. |
| 6,228,096 B1 | 5/2001 | Marchand |
| 6,231,605 B1 | 5/2001 | Ku |
| 6,231,615 B1 | 5/2001 | Preissman |
| 6,241,768 B1 | 6/2001 | Agarwal et al. |
| 6,245,080 B1 | 6/2001 | Levinson |
| 6,245,107 B1 | 6/2001 | Ferree |
| 6,248,106 B1 | 6/2001 | Ferree |
| 6,248,131 B1 | 6/2001 | Felt et al. |
| 6,258,094 B1 | 7/2001 | Nicholson et al. |
| 6,264,677 B1 | 7/2001 | Simon et al. |
| 6,267,772 B1 | 7/2001 | Mulhauser et al. |
| 6,280,453 B1 | 8/2001 | Kugel et al. |
| 6,287,324 B1 | 9/2001 | Yarnitsky et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,306,177 B1 | 10/2001 | Felt et al. |
| 6,312,448 B1 | 11/2001 | Bonutti |
| 6,319,263 B1 | 11/2001 | Levinson |
| 6,332,894 B1 | 12/2001 | Stalcup |
| 6,340,369 B1 | 1/2002 | Ferree |
| 6,342,064 B1 | 1/2002 | Koike et al. |
| 6,344,057 B1 | 2/2002 | Rabbe et al. |
| 6,344,058 B1 | 2/2002 | Ferree |
| 6,352,557 B1 | 3/2002 | Ferree |
| 6,355,052 B1 | 3/2002 | Neuss |
| 6,364,897 B1 | 4/2002 | Bonutti |
| 6,371,984 B1 | 4/2002 | Van Dyke et al. |
| 6,371,990 B1 | 4/2002 | Ferree |
| 6,391,060 B1 | 5/2002 | Ory et al. |
| 6,402,750 B1 | 6/2002 | Atkinson et al. |

(56) References Cited

U.S. PATENT DOCUMENTS

| | | |
|---|---|---|
| 6,402,784 B1 | 6/2002 | Wardlaw |
| 6,402,785 B1 | 6/2002 | Zdeblick |
| 6,409,739 B1 | 6/2002 | Nobles et al. |
| 6,419,676 B1 | 7/2002 | Zucherman et al. |
| 6,419,702 B1 | 7/2002 | Ferree |
| 6,419,703 B1 | 7/2002 | Fallin et al. |
| 6,419,704 B1 | 7/2002 | Ferree |
| 6,419,706 B1 | 7/2002 | Graf |
| 6,423,065 B2 | 7/2002 | Ferree |
| 6,423,080 B1 | 7/2002 | Gellman et al. |
| 6,425,919 B1 | 7/2002 | Lambrecht |
| 6,425,924 B1 | 7/2002 | Rousseau |
| 6,428,562 B2 | 8/2002 | Bonutti |
| 6,428,576 B1 | 8/2002 | Haldimann |
| 6,432,107 B1 | 8/2002 | Ferree |
| 6,432,123 B2 | 8/2002 | Schwartz et al. |
| 6,436,098 B1 | 8/2002 | Michelson |
| 6,436,099 B1 | 8/2002 | Drewry et al. |
| 6,436,143 B1 | 8/2002 | Ross et al. |
| 6,443,988 B2 | 9/2002 | Felt et al. |
| 6,447,531 B1 | 9/2002 | Amplatz |
| 6,452,924 B1 | 9/2002 | Golden et al. |
| 6,454,804 B1 | 9/2002 | Ferree |
| 6,464,712 B1 | 10/2002 | Epstein |
| 6,482,235 B1 | 11/2002 | Lambrecht et al. |
| 6,488,691 B1 | 12/2002 | Carroll et al. |
| 6,491,724 B1 | 12/2002 | Ferree |
| 6,494,883 B1 | 12/2002 | Ferree |
| 6,500,132 B1 | 12/2002 | Li |
| 6,500,184 B1 | 12/2002 | Chan et al. |
| 6,508,828 B1 | 1/2003 | Akerfeldt et al. |
| 6,508,839 B1 | 1/2003 | Lambrecht et al. |
| 6,511,488 B1 | 1/2003 | Marshall et al. |
| 6,511,498 B1 | 1/2003 | Fumex |
| 6,511,958 B1 | 1/2003 | Atkinson et al. |
| 6,514,255 B1 | 2/2003 | Ferree |
| 6,514,514 B1 | 2/2003 | Atkinson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,530,933 B1 | 3/2003 | Yeung et al. |
| 6,533,799 B1 | 3/2003 | Bouchier |
| 6,533,817 B1 | 3/2003 | Norton et al. |
| 6,544,267 B1 | 4/2003 | Cole et al. |
| 6,547,800 B2 | 4/2003 | Foerster et al. |
| 6,547,806 B1 | 4/2003 | Ding |
| 6,558,386 B1 | 5/2003 | Cragg |
| 6,558,390 B2 | 5/2003 | Cragg |
| 6,562,052 B2 | 5/2003 | Nobles et al. |
| 6,569,187 B1 | 5/2003 | Bonutti et al. |
| 6,569,442 B2 | 5/2003 | Gan et al. |
| 6,572,635 B1 | 6/2003 | Bonutti |
| 6,572,653 B1 | 6/2003 | Simonson |
| 6,575,979 B1 | 6/2003 | Cragg |
| 6,576,017 B2 | 6/2003 | Foley et al. |
| 6,579,291 B1 | 6/2003 | Keith et al. |
| 6,582,453 B1 | 6/2003 | Tran et al. |
| 6,592,608 B2 | 7/2003 | Fisher et al. |
| 6,592,609 B1 | 7/2003 | Bonutti |
| 6,592,625 B2 | 7/2003 | Cauthen |
| 6,596,012 B2 | 7/2003 | Akerfeldt et al. |
| 6,602,291 B1 | 8/2003 | Ray et al. |
| 6,605,096 B1 | 8/2003 | Ritchart |
| 6,607,541 B1 | 8/2003 | Gardiner et al. |
| 6,610,006 B1 | 8/2003 | Amid et al. |
| 6,610,071 B1 | 8/2003 | Cohn et al. |
| 6,610,079 B1 | 8/2003 | Li et al. |
| 6,610,091 B1 | 8/2003 | Reiley |
| 6,610,666 B1 | 8/2003 | Akerblom |
| 6,613,044 B2 | 9/2003 | Carl |
| 6,620,185 B1 | 9/2003 | Harvie et al. |
| 6,620,196 B1 | 9/2003 | Trieu |
| 6,623,492 B1 | 9/2003 | Berube et al. |
| 6,623,508 B2 | 9/2003 | Shaw et al. |
| 6,626,899 B2 | 9/2003 | Houser et al. |
| 6,626,916 B1 | 9/2003 | Yeung et al. |
| 6,635,073 B2 | 10/2003 | Bonutti |
| 6,645,227 B2 | 11/2003 | Fallin et al. |
| 6,645,247 B2 | 11/2003 | Ferree |
| 6,648,890 B2 | 11/2003 | Culbert et al. |
| 6,648,892 B2 | 11/2003 | Martello |
| 6,648,918 B2 | 11/2003 | Ferree |
| 6,648,919 B2 | 11/2003 | Ferree |
| 6,648,920 B2 | 11/2003 | Ferree |
| 6,652,561 B1 | 11/2003 | Tran |
| 6,652,585 B2 | 11/2003 | Lange |
| 6,656,182 B1 | 12/2003 | Hayhurst |
| 6,656,183 B2 | 12/2003 | Colleran et al. |
| 6,669,687 B1 | 12/2003 | Saadat |
| 6,669,707 B1 | 12/2003 | Swanstrom et al. |
| 6,669,729 B2 | 12/2003 | Chin |
| 6,673,088 B1 | 1/2004 | Vargas et al. |
| 6,676,665 B2 | 1/2004 | Foley et al. |
| 6,679,887 B2 | 1/2004 | Nicholson et al. |
| 6,679,914 B1 | 1/2004 | Gabbay |
| 6,684,886 B1 | 2/2004 | Alleyne |
| 6,685,695 B2 | 2/2004 | Ferree |
| 6,685,728 B2 | 2/2004 | Sinnott et al. |
| 6,689,125 B1 | 2/2004 | Keith et al. |
| 6,692,506 B1 | 2/2004 | Ory et al. |
| 6,695,858 B1 | 2/2004 | Dubrul et al. |
| 6,696,073 B2 | 2/2004 | Boyce |
| 6,699,263 B2 | 3/2004 | Cope |
| 6,706,068 B2 | 3/2004 | Ferree |
| 6,712,836 B1 | 3/2004 | Berg et al. |
| 6,712,837 B2 | 3/2004 | Akerfeldt et al. |
| 6,712,853 B2 | 3/2004 | Kuslich |
| 6,716,216 B1 | 4/2004 | Boucher et al. |
| 6,716,234 B2 | 4/2004 | Grafton et al. |
| 6,719,761 B1 | 4/2004 | Reiley et al. |
| 6,719,773 B1 | 4/2004 | Boucher et al. |
| 6,719,797 B1 | 4/2004 | Ferree |
| 6,723,058 B2 | 4/2004 | Li |
| 6,723,095 B2 | 4/2004 | Hammerslag |
| 6,723,097 B2 | 4/2004 | Fraser et al. |
| 6,723,107 B1 | 4/2004 | Skiba et al. |
| 6,723,133 B1 | 4/2004 | Pajotin |
| 6,723,335 B1 | 4/2004 | Moehlenbruck et al. |
| 6,726,721 B2 | 4/2004 | Stoy et al. |
| 6,730,092 B2 | 5/2004 | Songer |
| 6,730,112 B2 | 5/2004 | Levinson |
| 6,733,531 B1 | 5/2004 | Trieu |
| 6,733,534 B2 | 5/2004 | Sherman |
| 6,736,815 B2 | 5/2004 | Ginn |
| 6,740,093 B2 | 5/2004 | Hochschuler et al. |
| 6,743,255 B2 | 6/2004 | Ferree |
| 6,752,831 B2 | 6/2004 | Sybert et al. |
| 6,758,863 B2 | 7/2004 | Estes |
| 6,761,720 B1 | 7/2004 | Senegas |
| 6,761,722 B2 | 7/2004 | Cole et al. |
| 6,764,514 B1 | 7/2004 | Li et al. |
| 6,767,037 B2 | 7/2004 | Wenstrom |
| 6,770,076 B2 | 8/2004 | Foerster |
| 6,773,436 B2 | 8/2004 | Donnelly et al. |
| 6,773,699 B1 | 8/2004 | Soltz et al. |
| 6,780,198 B1 | 8/2004 | Gregoire et al. |
| 6,783,546 B2 | 8/2004 | Zuckerman et al. |
| 6,805,695 B2 | 10/2004 | Keith et al. |
| 6,805,697 B1 | 10/2004 | Helm et al. |
| 6,805,715 B2 | 10/2004 | Reuter et al. |
| 6,812,211 B2 | 11/2004 | Slivka et al. |
| 6,821,276 B2 | 11/2004 | Lambrecht et al. |
| 6,824,562 B2 | 11/2004 | Mathis et al. |
| 6,827,716 B2 | 12/2004 | Ryan et al. |
| 6,827,743 B2 | 12/2004 | Eisermann et al. |
| 6,830,570 B1 | 12/2004 | Frey et al. |
| 6,833,006 B2 | 12/2004 | Foley et al. |
| 6,835,205 B2 | 12/2004 | Atkinson et al. |
| 6,835,207 B2 | 12/2004 | Zacouto et al. |
| 6,835,208 B2 | 12/2004 | Marchosky |
| 6,841,150 B2 | 1/2005 | Halvorsen et al. |
| 6,843,799 B2 | 1/2005 | Bartlett |
| 6,852,128 B2 | 2/2005 | Lange |
| 6,860,895 B1 | 3/2005 | Akerfeldt et al. |

(56) References Cited

U.S. PATENT DOCUMENTS

| | | |
|---|---|---|
| 6,878,155 B2 | 4/2005 | Sharkey et al. |
| 6,878,167 B2 | 4/2005 | Ferree |
| 6,883,520 B2 | 4/2005 | Lambrecht et al. |
| 6,893,462 B2 | 5/2005 | Buskirk et al. |
| 6,896,675 B2 | 5/2005 | Leung et al. |
| 6,911,034 B2 | 6/2005 | Nobles et al. |
| 6,913,622 B2 | 7/2005 | Gjunter |
| 6,923,823 B1 | 8/2005 | Bartlett et al. |
| 6,932,833 B1 | 8/2005 | Sandoval et al. |
| 6,936,070 B1 | 8/2005 | Muhanna |
| 6,936,072 B2 | 8/2005 | Lambrecht et al. |
| 6,960,215 B2 | 11/2005 | Olson, Jr. et al. |
| 6,964,674 B1 | 11/2005 | Matsuura et al. |
| 6,966,910 B2 | 11/2005 | Ritland |
| 6,966,931 B2 | 11/2005 | Huang |
| 6,969,404 B2 | 11/2005 | Ferree |
| 6,972,027 B2 | 12/2005 | Fallin et al. |
| 6,974,479 B2 | 12/2005 | Trieu |
| 6,980,862 B2 | 12/2005 | Fredricks et al. |
| 6,984,241 B2 | 1/2006 | Lubbers et al. |
| 6,984,247 B2 | 1/2006 | Cauthen |
| 6,997,956 B2 | 2/2006 | Cauthen |
| 7,001,431 B2 | 2/2006 | Bao et al. |
| 7,004,959 B2 | 2/2006 | Bonutti |
| 7,004,970 B2 | 2/2006 | Cauthen |
| 7,033,393 B2 | 4/2006 | Gainor et al. |
| 7,033,395 B2 | 4/2006 | Cauthen |
| 7,037,334 B1 | 5/2006 | Hlavka et al. |
| 7,052,516 B2 | 5/2006 | Cauthen, III et al. |
| 7,083,638 B2 | 8/2006 | Foerster |
| 7,094,258 B2 | 8/2006 | Lambrecht et al. |
| 7,147,651 B2 | 12/2006 | Morrison et al. |
| 7,189,235 B2 | 3/2007 | Cauthen |
| 7,217,279 B2 | 5/2007 | Reese |
| 7,223,289 B2 | 5/2007 | Trieu et al. |
| 7,280,865 B2 | 10/2007 | Adler |
| 7,285,124 B2 | 10/2007 | Foerster |
| 7,306,417 B2 | 12/2007 | Dorstewitz |
| 7,309,337 B2 | 12/2007 | Colleran et al. |
| 7,318,840 B2 | 1/2008 | McKay |
| 7,320,701 B2 | 1/2008 | Haut et al. |
| 7,322,978 B2 | 1/2008 | West, Jr. |
| 7,329,272 B2 | 2/2008 | Burkhart et al. |
| 7,331,982 B1 | 2/2008 | Kaiser et al. |
| 7,344,539 B2 | 3/2008 | Serhan et al. |
| 7,367,978 B2 | 5/2008 | Drewry et al. |
| 7,371,253 B2 | 5/2008 | Leung et al. |
| 7,390,332 B2 | 6/2008 | Selvitelli et al. |
| 7,399,018 B1 | 7/2008 | Khachaturian |
| 7,410,489 B2 | 8/2008 | Dakin et al. |
| 7,445,634 B2 | 11/2008 | Trieu |
| 7,465,308 B2 | 12/2008 | Sikora et al. |
| 7,494,496 B2 | 2/2009 | Swain et al. |
| 7,500,983 B1 | 3/2009 | Kaiser et al. |
| 7,513,911 B2 | 4/2009 | Lambrecht et al. |
| 7,524,333 B2 | 4/2009 | Lambrecht et al. |
| 7,556,640 B2 | 7/2009 | Foerster |
| 7,611,521 B2 | 11/2009 | Lubbers et al. |
| 7,651,509 B2 | 1/2010 | Bojarski et al. |
| 7,682,540 B2 | 3/2010 | Boyan et al. |
| 7,749,273 B2 | 7/2010 | Cauthen, III et al. |
| 7,758,611 B2 | 7/2010 | Kato |
| 7,766,915 B2 | 8/2010 | Jackson |
| 7,766,923 B2 | 8/2010 | Catanese et al. |
| 7,766,939 B2 | 8/2010 | Yeung et al. |
| 7,846,162 B2 | 12/2010 | Nelson et al. |
| 7,875,058 B2 | 1/2011 | Holmes, Jr. |
| 7,905,903 B2 | 3/2011 | Stone et al. |
| 7,910,124 B2 | 3/2011 | Boyan et al. |
| 7,938,847 B2 | 5/2011 | Fanton et al. |
| 7,955,388 B2 | 6/2011 | Jensen et al. |
| 8,002,830 B2 | 8/2011 | Boyan et al. |
| 8,021,367 B2 | 9/2011 | Bourke et al. |
| 8,038,920 B2 | 10/2011 | Denoziere et al. |
| RE43,143 E | 1/2012 | Hayhurst |
| 8,100,141 B2 | 1/2012 | Slupecki et al. |
| 8,128,698 B2 | 3/2012 | Bentley et al. |
| 8,142,808 B2 | 3/2012 | Boyan et al. |
| 8,163,022 B2 | 4/2012 | Bentley et al. |
| 8,202,305 B2 | 6/2012 | Reiley |
| 8,318,192 B2 | 11/2012 | Boyan et al. |
| 8,486,436 B2 | 7/2013 | Boyan et al. |
| 8,652,172 B2 | 2/2014 | Denham et al. |
| 8,895,073 B2 | 11/2014 | Boyan et al. |
| 9,155,543 B2 | 10/2015 | Walsh et al. |
| 9,737,294 B2 * | 8/2017 | Wales ............... A61B 17/7291 |
| 2001/0029399 A1 | 10/2001 | Ku |
| 2001/0041916 A1 | 11/2001 | Bonutti |
| 2001/0051816 A1 | 12/2001 | Enzerink et al. |
| 2002/0032483 A1 | 3/2002 | Nicholson et al. |
| 2002/0077701 A1 | 6/2002 | Kuslich |
| 2002/0082698 A1 | 6/2002 | Parenteau et al. |
| 2002/0111688 A1 | 8/2002 | Cauthen |
| 2002/0123807 A1 | 9/2002 | Cauthen, III |
| 2002/0133179 A1 | 9/2002 | McDevitt et al. |
| 2002/0147461 A1 | 10/2002 | Aldrich |
| 2002/0151979 A1 | 10/2002 | Lambrecht et al. |
| 2002/0173851 A1 | 11/2002 | McKay |
| 2002/0188297 A1 | 12/2002 | Dakin et al. |
| 2003/0008396 A1 | 1/2003 | Ku |
| 2003/0074075 A1 | 4/2003 | Thomas |
| 2003/0083662 A1 | 5/2003 | Middleton |
| 2003/0105489 A1 | 6/2003 | Eichhorn et al. |
| 2003/0125807 A1 | 7/2003 | Lambrecht et al. |
| 2003/0130669 A1 | 7/2003 | Damarati et al. |
| 2003/0130694 A1 | 7/2003 | Bojarski et al. |
| 2003/0153976 A1 | 8/2003 | Cauthen, III et al. |
| 2003/0158604 A1 | 8/2003 | Cauthen, III et al. |
| 2003/0181983 A1 | 9/2003 | Cauthen |
| 2003/0195514 A1 | 10/2003 | Trieu et al. |
| 2003/0195628 A1 | 10/2003 | Bao et al. |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0039392 A1 | 2/2004 | Trieu |
| 2004/0054414 A1 | 3/2004 | Trieu |
| 2004/0097980 A1 | 5/2004 | Ferree |
| 2004/0143329 A1 | 7/2004 | Ku |
| 2004/0153074 A1 | 8/2004 | Bojarski et al. |
| 2004/0162568 A1 | 8/2004 | Saadat et al. |
| 2004/0260397 A1 | 12/2004 | Lambrecht et al. |
| 2005/0033363 A1 | 2/2005 | Bojarski et al. |
| 2005/0033440 A1 | 2/2005 | Lambrecht et al. |
| 2005/0038519 A1 | 2/2005 | Lambrecht et al. |
| 2005/0049592 A1 | 3/2005 | Keith et al. |
| 2005/0049704 A1 | 3/2005 | Jackson |
| 2005/0049708 A1 | 3/2005 | Atkinson et al. |
| 2005/0060038 A1 | 3/2005 | Sammartin |
| 2005/0071003 A1 | 3/2005 | Ku |
| 2005/0106255 A1 | 5/2005 | Ku |
| 2005/0149197 A1 | 7/2005 | Cauthen |
| 2005/0159812 A1 | 7/2005 | Dinger, III et al. |
| 2005/0234512 A1 | 10/2005 | Nakao |
| 2005/0256582 A1 | 11/2005 | Ferree |
| 2005/0278025 A1 | 12/2005 | Ku et al. |
| 2005/0283246 A1 | 12/2005 | Cauthen, III et al. |
| 2006/0060038 A1 | 3/2006 | Sammartin |
| 2006/0084994 A1 | 4/2006 | Atkinson et al. |
| 2006/0100711 A1 | 5/2006 | Cauthen |
| 2006/0122608 A1 | 6/2006 | Fallin et al. |
| 2006/0129156 A1 | 6/2006 | Cauthen, III et al. |
| 2006/0129245 A1 | 6/2006 | Cauthen |
| 2006/0142864 A1 | 6/2006 | Cauthen |
| 2006/0161258 A1 | 7/2006 | Cauthen |
| 2006/0167553 A1 | 7/2006 | Cauthen |
| 2006/0173545 A1 | 8/2006 | Cauthen |
| 2006/0190042 A1 | 8/2006 | Stone et al. |
| 2006/0190085 A1 | 8/2006 | Cauthen |
| 2006/0241773 A1 | 10/2006 | Cauthen |
| 2006/0253152 A1 | 11/2006 | Evans et al. |
| 2006/0287731 A1 | 12/2006 | Cauthen, III et al. |
| 2007/0061012 A1 | 3/2007 | Cauthen, III |
| 2007/0061013 A1 | 3/2007 | Cauthen, III et al. |

(56) References Cited

U.S. PATENT DOCUMENTS

| | | |
|---|---|---|
| 2007/0071568 A1 | 3/2007 | Dorstewitz |
| 2007/0073407 A1 | 3/2007 | Cauthen et al. |
| 2007/0083236 A1 | 4/2007 | Sikora et al. |
| 2007/0088438 A1 | 4/2007 | Cauthen, III et al. |
| 2007/0100348 A1 | 5/2007 | Cauthen, III et al. |
| 2007/0100354 A1 | 5/2007 | Cauthen, III et al. |
| 2007/0118226 A1 | 5/2007 | Lambrecht et al. |
| 2007/0156244 A1 | 7/2007 | Cauthen |
| 2007/0156245 A1 | 7/2007 | Cauthen, III et al. |
| 2007/0185497 A1 | 8/2007 | Cauthen et al. |
| 2007/0185532 A1* | 8/2007 | Stone ............... A61B 17/0401 606/232 |
| 2007/0198021 A1 | 8/2007 | Wales |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0288041 A1 | 12/2007 | Cauthen |
| 2007/0299540 A1 | 12/2007 | Ku |
| 2008/0033561 A1 | 2/2008 | Cauthen |
| 2008/0082128 A1 | 4/2008 | Stone |
| 2008/0086138 A1 | 4/2008 | Stone et al. |
| 2008/0140092 A1 | 6/2008 | Stone et al. |
| 2008/0147127 A1 | 6/2008 | Tipirneni et al. |
| 2008/0255613 A1 | 10/2008 | Kaiser et al. |
| 2009/0024165 A1 | 1/2009 | Ferree |
| 2009/0036893 A1 | 2/2009 | Kartalian et al. |
| 2009/0062854 A1 | 3/2009 | Kaiser et al. |
| 2009/0131936 A1 | 5/2009 | Tipirneni et al. |
| 2009/0131991 A1* | 5/2009 | Tipirneni ............... A61B 17/683 606/301 |
| 2009/0138042 A1 | 5/2009 | Thal |
| 2009/0259260 A1 | 10/2009 | Bentley et al. |
| 2009/0306711 A1 | 12/2009 | Stone et al. |
| 2009/0306718 A1* | 12/2009 | Tipirneni ............... A61B 17/683 606/263 |
| 2009/0318961 A1 | 12/2009 | Stone et al. |
| 2010/0016892 A1 | 1/2010 | Kaiser et al. |
| 2010/0016894 A1 | 1/2010 | Houard et al. |
| 2010/0036389 A1 | 2/2010 | Schwartz |
| 2010/0198258 A1 | 8/2010 | Heaven |
| 2010/0318125 A1 | 12/2010 | Gerber et al. |
| 2011/0004242 A1 | 1/2011 | Stchur |
| 2011/0118780 A1 | 5/2011 | Holmes, Jr. |
| 2011/0118796 A1 | 5/2011 | Reiley et al. |
| 2011/0172682 A1 | 7/2011 | Brady et al. |
| 2011/0172701 A1 | 7/2011 | Wales et al. |
| 2011/0224729 A1 | 9/2011 | Baker et al. |
| 2011/0257652 A1 | 10/2011 | Roman |
| 2011/0295252 A1* | 12/2011 | Tipirneni ............... A61B 17/683 606/62 |
| 2012/0016426 A1 | 1/2012 | Robinson |
| 2012/0089193 A1 | 4/2012 | Stone et al. |
| 2012/0101502 A1 | 4/2012 | Kartalian et al. |
| 2012/0165864 A1 | 6/2012 | Hernandez et al. |
| 2012/0165938 A1* | 6/2012 | Denham ............ A61B 17/0401 623/13.14 |
| 2013/0012765 A1 | 1/2013 | Vemuri et al. |
| 2013/0012942 A1 | 1/2013 | Nelson et al. |
| 2013/0096611 A1 | 4/2013 | Sullivan |
| 2013/0211451 A1* | 8/2013 | Wales ............... A61B 17/0401 606/232 |
| 2013/0253581 A1 | 9/2013 | Robinson |
| 2014/0081325 A1 | 3/2014 | Sengun |
| 2014/0214080 A1* | 7/2014 | Wales ............... A61B 17/7291 606/232 |
| 2015/0351815 A1* | 12/2015 | Wales ............... A61F 2/08 606/323 |
| 2016/0038308 A1 | 2/2016 | Walsh et al. |

FOREIGN PATENT DOCUMENTS

| | | |
|---|---|---|
| EP | 0025706 | 3/1981 |
| EP | 0042953 | 1/1982 |
| EP | 0049978 | 4/1982 |
| EP | 0076409 | 4/1983 |
| EP | 0110316 | 6/1984 |
| EP | 0122902 | 10/1984 |
| EP | 0126570 | 11/1984 |
| EP | 0145577 | 6/1985 |
| EP | 0193784 | 9/1986 |
| EP | 1108401 | 6/2001 |
| EP | 1743587 | 1/2007 |
| EP | 1797827 | 6/2007 |
| EP | 1857055 | 11/2007 |
| GB | 2054383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/20939 | 5/1998 |
| WO | WO 98/22050 | 5/1998 |
| WO | WO 99/00074 | 1/1999 |
| WO | WO 99/02108 | 1/1999 |
| WO | WO 99/04720 | 2/1999 |
| WO | WO 99/16381 | 4/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |
| WO | WO 2007/135101 | 11/2007 |
| WO | WO 2009/100242 | 8/2009 |
| WO | WO 2010/088561 | 8/2010 |
| WO | WO 2013/119812 | 8/2013 |
| WO | WO 2014/117107 | 7/2014 |

OTHER PUBLICATIONS

Surgical Technique for "PRO-TOE™ VO Hammertoe Fixation System" by Wright Medical Technology, Inc. (12 pgs) (dated 2011 and retrieved on or about May 2015).

Surgical Technique for "Hammertoe PIP Joint Arthrodesis using Trim-It Spin Pin™ Fixation" by Arthrex, Inc. (4 pgs) (dated 2014 and retrieved on or about May 2015).

Camasta et al., Buried Kirschner-Wire Fixation for Hammertoe Arthrodesis, S.J. Miller (Ed.) Reconstructive Surgery of the Foot and Leg, Pod Inst (2008) pp. 5-8.

* cited by examiner

SYSTEMS AND METHODS FOR ORTHOPEDIC REPAIR

CROSS-REFERENCE TO RELATED APPLICATIONS

This application is the U.S. National Phase under 35 U.S.C. § 371 of International Application PCT/US2014/013242, filed Jan. 27, 2014, titled Systems and Methods for Orthopedic Repair, which claims priority benefit of U.S. Provisional Application Nos. 61/757,553, filed Jan. 28, 2013, and 61/914,341, filed Dec. 10, 2013, the entireties of all of which are hereby incorporated by reference herein.

BACKGROUND

Field

This application relates generally to implants for the repair of orthopedic deformities. More specifically, the application relates to devices and methods for stabilizing, supporting and compressing adjacent bones (e.g., phalanges) to eliminate motion and promote fusion.

Description of the Related Art

Bone or joint fusion surgery (e.g., arthrodesis) can be performed to relieve arthritis pain in the ankles, wrists, fingers, thumbs, spine and/or other joints. In arthrodesis, two bones on each end of a joint are fused, eliminating movement along the joint. Joint fusion surgery can be used in patients whose joints have eroded or have been destroyed or disfigured by osteoarthritis, rheumatoid arthritis, other forms of arthritis and/or other diseases or conditions (e.g., hammer toe). While a fused joint loses flexibility, it can provide benefits with respect to bearing weight, stability, reduction of pain and the like.

SUMMARY

According to some embodiments, an implant for correcting a deformity (e.g., hammer toe, contracted toe, mallet toe, claw toe or related orthopedic deformities or conditions of the foot or hand, deformities resulting from osteoarthritis, rheumatoid arthritis, other inflammatory diseases, accidents, generalized joint pain and/or other joint diseases) comprises an implant body comprising an internal lumen extending from a first end to a second end of the implant body, wherein the implant body having a wall that defines one or more internal lumens. In some embodiments, the implant body comprises a suture side hole or window extending through the wall of the implant body, wherein the suture side hole or window is positioned between the first and second ends of the implant body, and wherein the suture side hole or window provides access to the at least one internal lumen through an exterior of the implant body. In some embodiments, the implant further comprises a tension assembly comprising a first bone anchor (and/or another type of bone engaging member) and a second bone anchor (and/or another type engaging member), wherein the first and second bone anchors are configured to be placed on opposite sides of the implant body when the implant is assembled for use. In some embodiments, the tension assembly further comprises at least one adjustable suture loop coupling, directly or indirectly, the first bone anchor to the second bone anchor, wherein at least a portion of the at least one adjustable suture loop is positioned within the internal lumen of the implant body. In some embodiments, at least a portion of the suture loop is routed or otherwise positioned outside the body. In some embodiments, the suture loop comprises a suture line. In other embodiments, the suture loop comprises an elastomeric member or component. In some embodiments, the elastomeric member or component does not comprise a suture. In some embodiments, the at least one adjustable suture loop comprises at least one suture tail or free end that extends through the suture side hole and to an exterior of the implant body, wherein, upon deployment and fixation of the first and second bone anchors within bone bores of a subject and upon the application of tension to the at least one suture tail in a direction away from the implant body, a tension between the first and second bone anchors is increased and/or maintained (e.g., to bring adjacent bones secured to the implant closer and/or in contact with one another).

According to some embodiments, one or more both of the first and second bone anchors comprise an outer anchor tube and an insert, the anchor tube defining a longitudinal channel that receives the insert. In some embodiments, the outer anchor tube of the first and second bone anchors comprises a plurality of fingers, barbs or other engagement members. In one embodiment, such fingers, barbs or other engagement members are arranged radially at least partially around the outer anchor tube, wherein the fingers are configured to engage bone at an implantation site (e.g., bone bore). In some embodiments, at least one of the first and second bone anchors comprises an eyelet or securement element, wherein a portion of the at least one adjustable suture loop traverses through the eyelet or securement element to secure the at least one adjustable suture loop to the corresponding bone anchor. According to some embodiments, the implant body comprises a rigid, semi-rigid and/or flexible structure. In some embodiments, the implant body comprises one or more rigid, semi-rigid and/or flexible materials. In one embodiment, the implant body comprises one or more of the following: a polymeric material (e.g., polyether ether ketone or PEEK), a metal or alloy (e.g., stainless steel), an elastomeric material (e.g., rubber) and/or any other natural or synthetic material.

According to some embodiments, the implant additionally comprises a positioning element located along the implant body, the positioning element being configured to facilitate adjustment of the implant body within corresponding bone bores of a subject once the implant has been located therein. In some embodiments, the positioning system is incorporated with the tension system. In one embodiment, the positioning system includes at least a portion of the suture loop that comprises the tension system. In other embodiments, the positioning system is separate and distinct from the tension system.

According to some embodiments, the at least one adjustable suture loop comprises at least one knotless construct or system, wherein the at least one knotless construct or system includes a portion of the at least one adjustable suture loop routed through an interior of a section of the at least one adjustable suture loop to create at least one locking or friction section or portion. In some embodiments, the at least one locking or friction section or portion of the knotless suture system permits a surgeon to create and maintain tension in the implant. In one embodiment, the tension created and maintained within the implant using the knotless system does not require a surgeon to tie the suture system or otherwise secure the system separately from the knotless configuration. According to some embodiments, at least one of the first and second bone anchors comprises an eyelet or securement element, wherein a portion of the at least one adjustable suture loop traverses through the eyelet to secure the at least one adjustable suture loop to the first and second bone anchors. According to some embodiments, the implant body comprises a rigid, semi-rigid and/or flexible structure. In some embodiments, the implant body comprises one or more rigid, semi-rigid and/or flexible materials. In one embodiment, the implant body comprises one or more of the following: a polymeric material (e.g., polyether ether ketone or PEEK), a metal or alloy (e.g., stainless steel), an elastomeric material (e.g., rubber) and/or any other natural or synthetic material.

According to some embodiments, the at least one adjustable suture loop comprises at least one knotless construct or system, the at least one knotless construct or system comprising a portion of the at least one adjustable suture loop routed through an interior of a section of the at least one adjustable suture loop, wherein each of the first and second bone anchors comprises an eyelet or securement element, wherein a portion of the at least one adjustable suture loop traverses through the eyelet to secure the at least one adjustable suture loop to the first and second bone anchors. In some embodiments, the implant body comprises a polymer or other rigid, semi-rigid and/or flexible material (e.g., metal, elastomeric material, etc.). In some embodiments, the cross-sectional shape of the implant body is hexagonal or other polygonal shape (e.g., triangular, square or rectangular, pentagonal, octagonal, etc.).

According to some embodiments, the implant further comprises a sliding knot formed by the at least one adjustable suture loop, wherein the sliding knot is maintained within the interior lumen of the implant body. In some embodiments, an outer dimension (e.g., diameter or other cross-sectional dimension) of the sliding knot is greater than the diameter or other cross-sectional dimension of the suture side hole or window.

According to some embodiments, the implant body comprises at least one polymeric material, e.g., polyether ether ketone (PEEK), another polymeric material, etc. In other embodiments, the implant body comprises a metal or alloy (e.g. stainless steel, brass, etc.), an elastomeric material (e.g., rubber) and/or any other natural or synthetic materials, either in addition to or in lieu of at least one polymeric material. In some embodiments, the implant body comprises both a polymeric material (e.g., PEEK) and a metal or alloy (e.g., Nitinol, stainless steel, etc.).

According to some embodiments, at least one of the first and second bone anchors comprises a plurality of deflectable fingers, barbs or other expandable elements or members configured to engage bone at an implantation site. In some embodiments, at least one of the first and second bone anchors comprises an eyelet or securement element (e.g., positioned so that it faces the adjacent implant body), wherein a portion of the at least one adjustable suture loop traverses through the eyelet or securement element to secure the at least one adjustable suture loop to the first and second bone anchors.

According to some embodiments, the at least one adjustable suture loop comprises at least one knotless construct or design, wherein the at least one knotless construct comprises a portion of the at least one adjustable suture loop routed through an interior of a section of the at least one adjustable suture loop.

According to some embodiments, the cross-sectional shape of the implant body is polygonal (e.g., hexagonal, triangular, square or rectangular, pentagonal, octagonal, decagonal, etc.). In other embodiments, the cross-sectional shape of the implant body is at least partially circular, oval, curved, irregular and/or otherwise non-linear.

According to some embodiments, a length of the implant body is between 15 and 20 mm (e.g., 15, 16, 17, 18, 19, 20 mm). In other embodiment, the implant body is longer than 20 mm (e.g., 20-25 mm, 25-30 mm, 30-40 mm, 40-50 mm, more than 50 mm, etc.) or shorter than 15 mm (e.g., 10-15 mm, 5-10 mm, 0-5 mm, etc.). In some embodiments, an outer cross-section dimension (e.g., diameter) of the implant body is between 2 and 5 mm (e.g., 2, 3, 4, 5 mm). In other embodiments, the outer cross-section dimension (e.g., diameter) of the implant body is less than 2 mm (e.g., 0-0.5, 0.5-1, 1-1.5, 1.5-2 mm, etc.) or greater than 5 mm (e.g., 5-6, 6-7, 7-8, 8-9, 9-10, 10-15, 15-20 mm, more than 20 mm, etc.).

According to some embodiments, the implant body comprises at least one bend or angle along its length. In some embodiments, a bend or angle along the implant body helps provide a natural shape to the joint being treated (e.g. fused). In some embodiments, the angle or bend to the implant body is about 0 to 30 degrees (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 21-22, 22-23, 23-24, 24-25, 25-26, 26-27, 27-28, 28-29, 29-30 degrees, etc.). In some embodiments, the bend or angle along the implant body is greater than 30 degrees (e.g., 30-35, 35-40, 40-50 degrees, greater than 50 degrees, etc.).

According to some embodiments, the at least one adjustable suture loop comprises polyethylene and/or another polymeric material. In some embodiments, at least a portion of the suture loop is routed or otherwise positioned outside the body. In some embodiments, the suture loop comprises a suture line. In other embodiments, the suture loop comprises an elastomeric member or component. In some embodiments, the elastomeric member or component does not comprise a suture. In some embodiments, the at least one suture loop comprises a flexible and/or resilient material.

According to some embodiments, a proximal and/or distal portion of the implant body (e.g., along either side of a joint or other point of fusion) is configured to extend across two or more bones (e.g., phalanges). Thus, in some embodiments, an implant body is configured to span across three or more bones.

According to some embodiments, method of correcting a deformity in or near a joint of a subject (e.g., hammer toe, contracted toe, mallet toe, claw toe or related orthopedic deformities or conditions of the foot or hand, deformities resulting from osteoarthritis, rheumatoid arthritis, other inflammatory diseases, accidents, generalized joint pain and/or other joint diseases) comprises positioning a first bone anchor o an implant into a first bore located in a proximal bone (e.g., proximal phalange) of the subject, positioning a second bone anchor of the implant into a second bore located in a distal bone (e.g., proximal or intermediate phalange) of the subject, deploying the first and second bone anchors so that the first and second bone anchors engage adjacent bone tissue, positioning a proximal end of the implant body into the first bore of the proximal bone, positioning a distal end of the implant body into the second bore of the distal bone and manipulating the at least one suture tail of the at least one adjustable suture loop to increase a tension between the first and second bone anchors. In some embodiments, increasing a tension between the first and second bone anchors creates compression between the proximal and distal bone to promote fusion.

According to some embodiments, manipulating the at least one suture tail of the at least one adjustable suture loop comprises moving the at least one suture tail away from the implant body. In some embodiments, the suture tail or free end is routed at least partially between the outside of the implant body and the inside of the bone bore, such that the suture tail or free end is positioned through a bore to the joint and/or through a longitudinal opening of the bone opposite of the joint.

According to some embodiments, the method further includes moving the implant body further within the first bore or the second bore (e.g., proximally and/or distally) prior to manipulating the at least one suture tail. In some embodiments, moving the implant body further within the first bore or the second bore comprises manipulating a positioning element of the implant body. In one embodiment, the positioning element includes the at least one suture tail of the at least one adjustable suture loop. In other embodiments, the positioning element is separate and distinct from the tension system of the implant.

According to some embodiments, the method further comprises preparing adjacent surfaces of the joint prior to implanting the implant therein, wherein preparing adjacent surfaces of the joint comprises resecting bone tissue (e.g., using a rasp to at least partially remove bone and/or cartilage tissue along the bone(s) adjacent the targeted joint) and/or drilling the first and second bores with in the bones. In some embodiments, the method further includes providing at least one graft material and/or other bone-fusion promoting material or components at or near the joint, before, during or after implantation of the implant within the targeted joint.

According to some embodiments, deploying the first and second bone anchors comprises radially expanding a plurality of deflectable fingers, barbs or members of each bone anchor. In one embodiment, the at least one adjustable suture loop comprises at least one knotless construct or design, wherein the at least one knotless construct or design comprises a portion of the at least one adjustable suture loop routed through an interior of a section of the at least one adjustable suture loop.

According to some embodiments, a method of correcting a deformity in or near a joint of a subject (e.g., hammer toe, contracted toe, mallet toe, claw toe or related orthopedic deformities or conditions of the foot or hand, deformities resulting from osteoarthritis, rheumatoid arthritis, other inflammatory diseases, accidents, generalized joint pain and/or other joint diseases) comprises positioning a first bone anchor of an implant into a first bore located in a proximal bone of the subject, wherein the implant comprises an implant body having an internal lumen, a suture window extending through a wall of the implant body, the suture window providing access to the internal lumen through an exterior of the implant body. In some embodiments, the implant further comprises a tension assembly having the first bone anchor and a second bone anchor, wherein the first and second bone anchors are located on opposite sides of the implant body. In one embodiment, the tension assembly further comprises at least one adjustable suture loop coupling the first bone anchor to the second bone anchor, wherein at least a portion of the at least one adjustable suture loop is positioned at least partially within the internal lumen of the implant body, the at least one adjustable suture loop further comprising at least one suture tail that extends through the suture window and to an exterior of the implant body. In some embodiments, the method further includes positioning the second bone anchor of the implant into a second bore located in a distal bone of the subject and deploying the first and second bone anchors so that the first and second bone anchors engage adjacent bone tissue of the proximal and distal bones. In some embodiments, the method additionally comprises positioning a proximal end of the implant body into the first bore of the proximal bone, positioning a distal end of the implant body into the second bore of the distal bone and applying tension to the at least one suture tail of the at least one adjustable suture loop to create compression between the proximal and distal bone to promote fusion.

According to some embodiments, applying tension to the at least one suture tail of the at least one adjustable suture loop comprises moving the at least one suture tail away from the implant body. In some embodiments, the method further includes moving the implant body further within the first bore or the second bore prior to manipulating the at least one suture tail. In one embodiment, moving the implant body further within the first bore or the second bore comprises manipulating a positioning element of the implant body. In some embodiments, positioning element includes the at least one suture tail of the at least one adjustable suture loop. In some embodiments, the method further comprises preparing adjacent surfaces of the joint prior to implanting the implant therein, wherein preparing adjacent surfaces of the joint comprises resecting bone tissue along the joint and drilling the first and second bores.

According to some embodiments, deploying the first and second bone anchors comprises radially expanding a plurality of deflectable fingers of each bone anchor. In some embodiments, the at least one adjustable suture loop comprises at least one knotless construct or design, wherein the at least one knotless construct or design comprises a portion of the at least one adjustable suture loop routed through an interior of a section of the at least one adjustable suture loop.

According to some embodiments, an implant for correcting a deformity in or near a joint of a subject comprises an implant body comprising a lumen extending from a first end to a second end of the implant body, wherein the implant body comprises a window extending through a wall of the implant body, the window being positioned between the first and second ends of the implant body, and wherein the window provides access to the internal lumen through an exterior of the implant body. In some embodiments, the implant further includes a tension assembly comprising a first bone anchor, a second bone anchor and at least one adjustable suture loop coupling the first bone anchor to the second bone anchor, wherein the implant body is positioned between the first and second bone anchors, and wherein at least a portion of the at least one adjustable suture loop is positioned within the internal lumen of the implant body. In some embodiments, the at least one adjustable suture loop comprises at least one suture tail that extends to an exterior of the implant body through the window, wherein, upon deployment and fixation of the first and second bone anchors within bone bores of a subject and upon the application of tension to the at least one suture tail in a direction away from the implant body, a tension between the first and second bone anchors is increased, and wherein the at least one adjustable suture loop comprises at least one knotless construct, the at least one knotless construct comprising a portion of the at least one adjustable suture loop routed through an interior of a section of the at least one adjustable suture loop.

According to some embodiments, the at least one adjustable suture loop comprises at least one knotless construct or system, the at least one knotless construct or system comprising a portion of the at least one adjustable suture loop routed through an interior of a section of the at least one adjustable suture loop, wherein each of the first and second bone anchors comprises an eyelet or securement element, wherein a portion of the at least one adjustable suture loop traverses through the eyelet to secure the at least one adjustable suture loop to the first and second bone anchors. In some embodiments, the implant body comprises a polymer or other rigid, semi-rigid and/or flexible material (e.g., metal, elastomeric material, etc.). In some embodiments, the cross-sectional shape of the implant body is hexagonal or other polygonal shape (e.g., triangular, square or rectangular, pentagonal, octagonal, etc.).

According to some embodiments, the implant further comprises a sliding knot formed by the at least one adjustable suture loop, wherein the sliding knot is maintained within the interior lumen of the implant body. In some embodiments, an outer dimension (e.g., diameter or other cross-sectional dimension) of the sliding knot is greater than the diameter or other cross-sectional dimension of the suture side hole or window.

According to some embodiments, the implant body comprises at least one polymeric material, e.g., polyether ether ketone (PEEK), another polymeric material, etc. In other embodiments, the implant body comprises a metal or alloy (e.g. stainless steel, brass, etc.), an elastomeric material (e.g., rubber) and/or any other natural or synthetic materials, either in addition to or in lieu of at least one polymeric material.

According to some embodiments, at least one of the first and second bone anchors comprises a plurality of deflectable fingers, barbs or other expandable elements or members configured to engage bone at an implantation site. In some embodiments, at least one of the first and second bone anchors comprises an eyelet or securement element (e.g., positioned so that it faces the adjacent implant body), wherein a portion of the at least one adjustable suture loop traverses through the eyelet or securement element to secure the at least one adjustable suture loop to the first and second bone anchors.

According to some embodiments, the at least one adjustable suture loop comprises at least one knotless construct or design, wherein the at least one knotless construct comprises a portion of the at least one adjustable suture loop routed through an interior of a section of the at least one adjustable suture loop.

According to some embodiments, the cross-sectional shape of the implant body is polygonal (e.g., hexagonal, triangular, square or rectangular, pentagonal, octagonal, decagonal, etc.). In other embodiments, the cross-sectional shape of the implant body is at least partially circular, oval, curved, irregular and/or otherwise non-linear.

According to some embodiments, a length of the implant body is between 15 and 20 mm (e.g., 15, 16, 17, 18, 19, 20 mm). In other embodiment, the implant body is longer than 20 mm (e.g., 20-25 mm, 25-30 mm, 30-40 mm, 40-50 mm, more than 50 mm, etc.) or shorter than 15 mm (e.g., 10-15 mm, 5-10 mm, 0-5 mm, etc.). In some embodiments, an outer cross-section dimension (e.g., diameter) of the implant body is between 2 and 5 mm (e.g., 2, 3, 4, 5 mm). In other embodiments, the outer cross-section dimension (e.g., diameter) of the implant body is less than 2 mm (e.g., 0-0.5, 0.5-1, 1-1.5, 1.5-2 mm, etc.) or greater than 5 mm (e.g., 5-6, 6-7, 7-8, 8-9, 9-10, 10-15, 15-20 mm, more than 20 mm, etc.).

According to some embodiments, the implant body comprises at least one bend or angle along its length. In some embodiments, a bend or angle along the implant body helps provide a natural shape to the joint being treated (e.g. fused). In some embodiments, the angle or bend to the implant body is about 0 to 30 degrees (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 21-22, 22-23, 23-24, 24-25, 25-26, 26-27, 27-28, 28-29, 29-30 degrees, etc.). In some embodiments, the bend or angle along the implant body is greater than 30 degrees (e.g., 30-35, 35-40, 40-50 degrees, greater than 50 degrees, etc.).

According to some embodiments, the at least one adjustable suture loop comprises polyethylene and/or another polymeric material. In some embodiments, at least a portion of the suture loop is routed or otherwise positioned outside the body. In some embodiments, the suture loop comprises a suture line. In other embodiments, the suture loop comprises an elastomeric member or component. In some embodiments, the elastomeric member or component does not comprise a suture. In some embodiments, the at least one suture loop comprises a flexible and/or resilient material.

According to some embodiments, the implant body and/or the bone anchors, are provided in a variety of sizes and shapes to accommodate for different indications, applications, subject and/or the like. Such implant bodies and/or anchors can be provided to the surgeon or other user in a kit. For example, a kit can include implant bodies of varying lengths and/or cross-sectional dimensions. In some embodiments, a kit includes bone anchors of different diameters or sizes, implants of varying cross-sectional dimensions and/or lengths and suture loops of varying designs, sizes, lengths and/or other properties. Thus, a surgeon or other practitioner can advantageously customize a procedure by combining various components. This can help provide for a more successful treatment procedure by using components that are best sized, shaped and/or otherwise configured for a specific application or use. In other embodiments, the implant body is configured be cut or otherwise reshaped in order to modify the implant for a particular use or application. Thus, is some embodiments, the implant body is provided in one or more lengths that can be shortened. In some embodiments, the implant body comprises materials and/or a configuration that is configured to be cut or otherwise shortened. For example, in some embodiments, the implant body can include segments that are scored, perforated, undermined and/or otherwise configured to be cut along certain predetermined locations.

According to some embodiments, a method of correcting a deformity in or near a joint of a subject comprises providing an implant, wherein the implant comprises an implant body having an internal lumen, a window extending through a wall of the implant body, the window providing access to the internal lumen, wherein the implant further comprises a tension assembly having a first bone anchor and a second bone anchor, wherein the implant body is positioned generally between the first and second bone anchors. In some embodiments, the tension assembly further comprises at least one adjustable suture loop coupling the first bone anchor to the second bone anchor, wherein at least a portion of the at least one adjustable suture loop is positioned at least partially within the internal lumen of the implant body, the at least one adjustable suture loop further comprising at least one suture free end that extends through the window and to an exterior of the implant body. In some embodiments, the second bone anchor of the implant is configured to be positioned into a second bore located in a distal bone of the subject, wherein the first and second bone anchors are configured to be radially expanded so that the first and second bone anchors engage adjacent bone tissue of the proximal and distal bones. In one embodiment, a proximal end of the implant body is configured to be positioned within the first bore of the proximal bone, wherein a distal end of the implant body is configured to be positioned within the second bore of the distal bone. In some embodiments, upon an application of tension to the at least one suture free end of the at least one adjustable suture loop is configured to create compression between the proximal and distal bone to promote fusion by creating and sustaining tension between the first and second bone anchors.

According to some embodiments, the implant body is configured to be selectively moved further within the first bore or the second bore (e.g., distally or proximally) by manipulating a positioning element of the implant body. In some embodiments, the positioning element includes the at least one suture free end of the at least one adjustable suture loop. In some embodiments, the first and second bone anchors are configured to be expanded by radial deployment of a plurality of deflectable fingers of each bone anchor. In one embodiment, the at least one adjustable suture loop comprises at least one knotless construct, wherein the at least one knotless construct comprises a portion of the at least one adjustable suture loop routed through an interior of a section of the at least one adjustable suture loop.

The methods summarized above and set forth in further detail below describe certain actions taken by a practitioner; however, it should be understood that they can also include the instruction of those actions by another party. Thus, actions such as "positioning a proximal or distal end of the implant body" include "instructing positioning a proximal or distal end of the implant body."

BRIEF DESCRIPTION OF THE DRAWINGS

These and other features, aspects and advantages of the present application are described with reference to drawings of certain embodiments, which are intended to illustrate, but not to limit, the various inventions disclosed herein. It is to be understood that the attached drawings are for the purpose of illustrating concepts and embodiments of the present application and may not be to scale.

DETAILED DESCRIPTION

The discussion and the figures illustrated and referenced herein describe various embodiments of an implant, as well as various tools, systems and methods related thereto. A number of these devices and associated treatment methods are particularly well suited to treat hammer toe, contracted toe, mallet toe, claw toe or related orthopedic deformities or conditions of the foot. Such implants are configured to secure to adjacent phalanges or other bones in a subject's foot or hand (or to another anatomical area of the subject, e.g., wrists, cervical and/or other portions of the spine, other small joints, etc.) and to promote fusion or arthrodesis by reliably maintaining the adjacent bone surfaces in compressive contact with each other over time. Such embodiments can be used to treat deformities resulting from hammer toe, osteoarthritis, rheumatoid arthritis, other inflammatory diseases, accidents, generalized joint pain and/or other joint diseases. However, the various devices, systems, methods and other features of the embodiments disclosed herein may be utilized or applied to other types of apparatuses, systems, procedures and/or methods, including arrangements that have non-medical benefits or applications.

Figure 1:
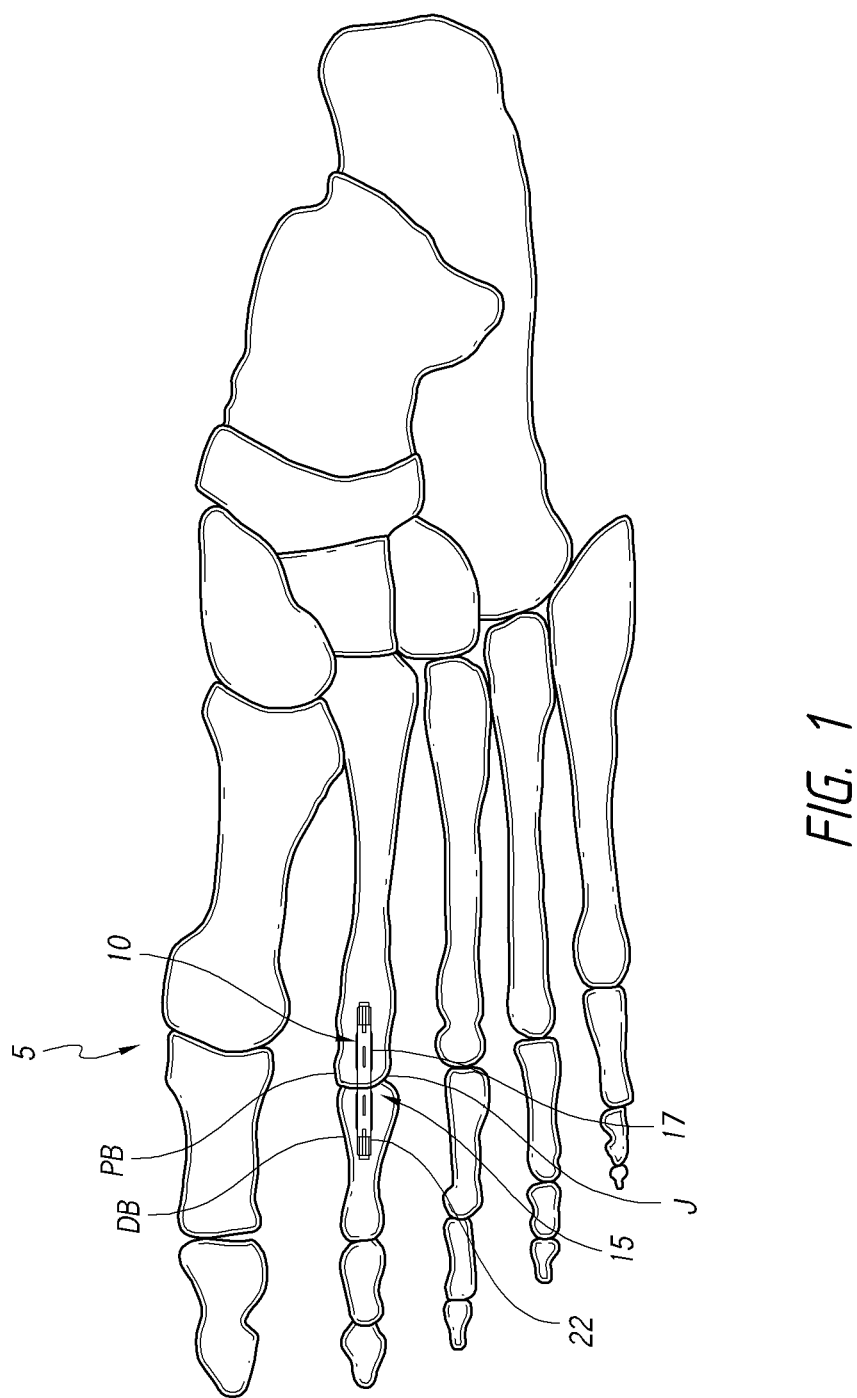
FIG. 1 illustrates a skeletal system of a human foot with an implant according to one embodiment implanted to treat a joint deformity.

FIG. 1 illustrates a skeletal system 5 of a human foot F with an implant 100 according to an embodiment disclosed in the present application in an implanted state to treat a joint deformity (e.g., hammer toe) or another condition (e.g., other joint disease, fracture, etc.) of a subject. As shown and as discussed in greater detail herein, the implant 10 can be configured span a joint J (e.g., a proximal interphalangeal joint, other joint of the foot or hand, wrist, spine, etc.) and can include a proximal portion 17 disposed and secured within a proximal bone PB (e.g., a proximal phalange), and a distal portion 22 disposed and secured within a distal bone DB (e.g., an intermediate phalange). According to some embodiments, an implant 100 can help re-align adjacent bones (e.g., across a joint) or bone portions (e.g., across a fracture), such as, for example, proximal and intermediate phalanges PB, DB. Thus, the implant 10 can assist in permanently fusing and/or otherwise stabilizing a joint J. In addition, as described in further detail herein, the implant 10 can be configured to urge the adjacent bones or bone portions (e.g., proximal and intermediate phalanges, PB, DB) toward one another and apply compression to the joint J (e.g., interphalangeal joint), thereby further enhancing joint stability and encouraging rapid arthrodesis or fusion of the bones at the joint 15.

According to some embodiments, an implantable orthopedic repair implant comprises two or more elements, including, for example, an implant body and a tension assembly, which includes one or more bone anchors and/or other bone engaging members or features. The implant body can include a rigid tubular support element that provides stability to help join two adjacent bones. In some embodiments, the implant body comprises one or more rigid polymers, other biocompatible, bioresorbable and/or osteoinductive materials and/or any other materials. In one embodiment, the implant body and/or any other portion of an implant can include one or more radiolucent portions or components. In some embodiments, the implant body comprises one or more metals (e.g., stainless steel), alloys, other natural and/or synthetic materials, elastomeric materials and/or the like. In other embodiments, the implant body can comprises one or more flexible and/or semi-rigid materials, either in lieu of or in addition to rigid materials, as desired or required.

According to some embodiments, the implant body comprises one or more internal lumens, at least partially through which one or more portions of a tension assembly can be positioned. In some embodiments, the implant body includes ribs or similar features that extend at least partially along the length of the body in a longitudinal direction. Such ribs or other features can help improve the rigidity of the implant, prevent rotational movement once embedded into bone and/or provide one or more other advantages or benefits to the implant. In some embodiments, the cross-sectional shape of the implant body can vary, as desired or required for a particular application or use. For example, the cross-sectional shape can be circular, oval, triangular, square or other rectangular, pentagonal, hexagonal, octagonal, other polygonal, irregular and/or the like. In one embodiment, the implant body comprises a hexagonal cross-sectional shape that takes advantage of the exterior corners formed by adjacent sides of the body to help secure the implant body within an implant site. Such configurations can help prevent rotation or other movement in a target anatomical location (e.g., joint) after implantation.

As described in greater detail herein, the tension assembly can include an adjustable suture loop that is secured to bone anchoring elements (e.g., bone anchors, other bone-engaging members, etc.) positioned along opposite sides (e.g., on either side of a sliding knot). The suture loop, sliding knot and/or one or more other components of the tension assembly can extend at least partially within the implant body (e.g., within a lumen of the implant body). Such embodiments of an implant advantageously permit surgeons to place anchors into adjacent bones (or bone portions), position the implant body into such bones (or bone portions) and subsequently manipulate a tension assembly to draw the bones or bone portions to each other. Thus, as described in greater detail herein, the suture loop of the tension assembly can help draw two bones anchors toward one another to create compression between the two adjacent bones. The support, stability and compression help promote healing and bone growth and thereby enhance a fusion or arthrodesis procedure.

According to some embodiments, the tensioning of the suture loop of the tension assembly includes pulling on one or more suture tails or ends of the suture assembly. In turn, this can shorten the suture loop between the opposing bone anchors to draw on or both of the anchors closer to the implant body that is generally positioned between the anchors. In some embodiments, the bone anchors can comprises one or more fingers, barbs and/or other engaging members to help secure the bone anchor to adjacent tissue of the subject's bone. As discussed with reference to several embodiments disclosed herein, the implant body can include a suture hole or window that runs through a side wall (e.g., in some arrangements, orthogonally, perpendicularly, diagonally or at some desired angle relative to a lumen of the implant body). Such a side hole or window can form an internal wall which acts as an internal knot pusher for the sliding knot of the tension assembly. The side hole or window can advantageously permit one or more strands of the suture system to exit the interior lumen of the implant body so as to permit a surgeon or other practitioner to access and manipulate the suture system during an implantation procedure. Thus, in some embodiments, the outer diameter (or other cross-sectional dimension) of the sliding knot is larger than the suture side hole or window to ensure the sliding knot remains advantageously fixed within the lumen of the implant body.

Figure 2A:
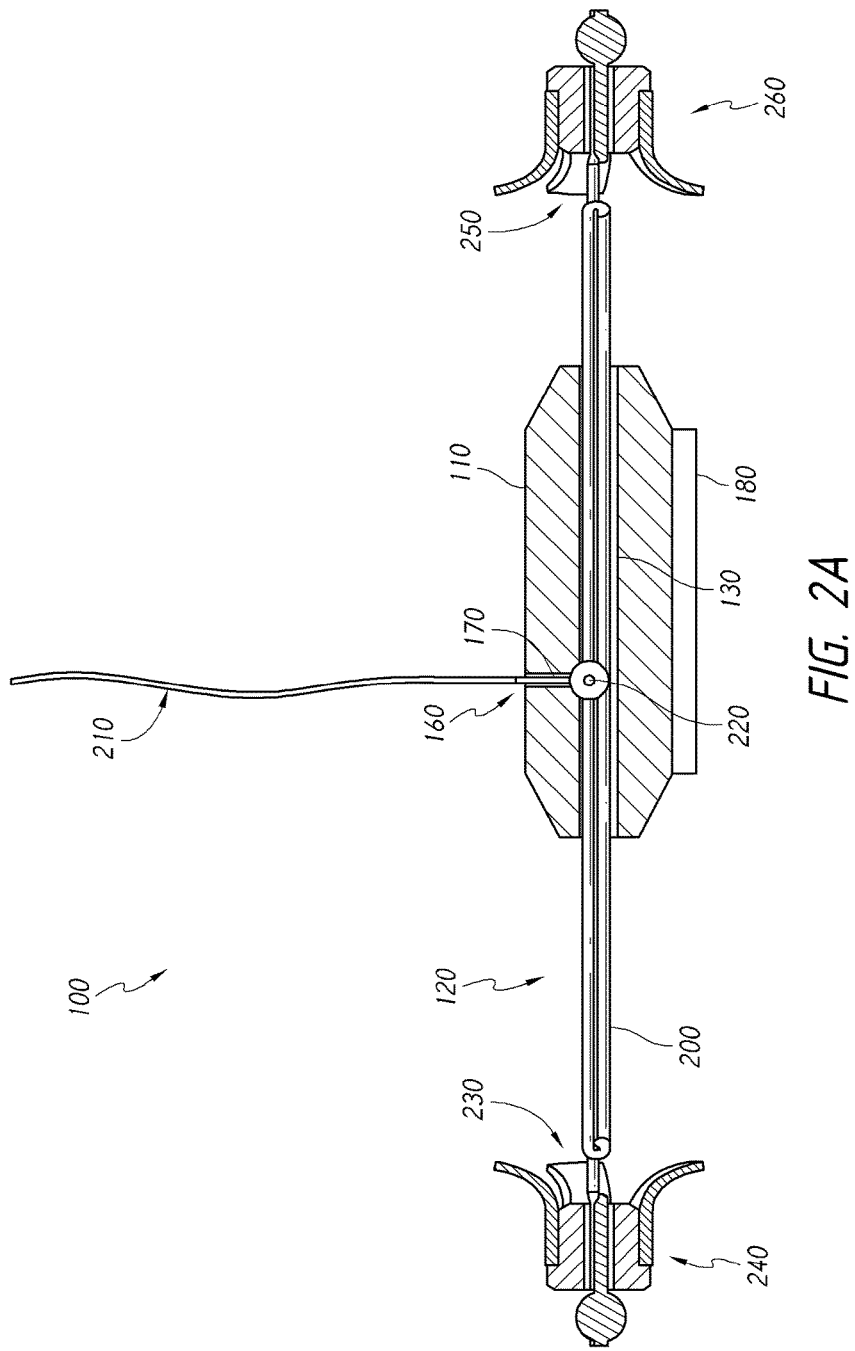
FIG. 2A illustrates a cross-sectional view of an embodiment of an orthopedic repair implant.
Figure 2B:
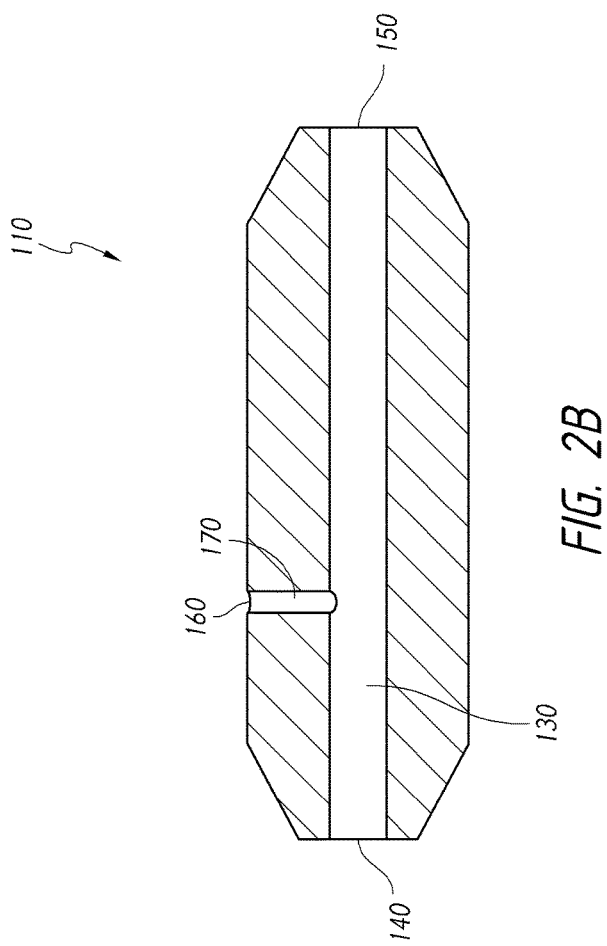
FIG. 2B illustrates a cross-sectional view of the implant body of the implant of FIG. 2A.

FIG. 2A illustrates a cross-sectional view of one embodiment of an orthopedic implant 100 that comprises an implant body 110 and a tension assembly 120. As shown in FIGS. 2A and 2B, the implant body 110 can include a generally tubular shape which defines an inner lumen 130 extending longitudinally through the implant body 110 (e.g., along a central or major longitudinal axis). In some embodiments, the cross-sectional shape of the implant body can vary, as desired or required for a particular application or use. For example, the cross-sectional shape can be circular, oval, triangular, square or other rectangular, pentagonal, hexagonal, octagonal, other polygonal, irregular and/or the like. In one embodiment, the implant body comprises a hexagonal cross-sectional shape that takes advantage of the exterior corners formed by adjacent sides of the body to help secure the implant body within an implant site. Such configurations can help prevent rotation or other movement in a target anatomical location (e.g., joint) after implantation. The lumen 130 can extend form first and second open ends 140, 150 of the implant body 110. In some embodiments, the implant body 110 comprises one or more rigid polymeric materials, such as, for example, polyether ether ketone (PEEK) polyphenylene, polysulfone, polyethylene, and the like. However, in other embodiments, the implant body includes one or more other materials, including other rigid materials and/or semi-rigid and/or flexible materials, as desired or required by a particular application or use, such as for example, other polymeric materials, metals, alloys, other synthetic or natural materials and/or the like.

With continued reference to FIGS. 2A and 2B, the implant body 110 can include a suture side hole or window 160 that extends from the inner lumen 130 to the exterior of the implant body 110. Such a side hole or window 160, which permits access to the inner lumen 130 from the exterior of the implant body, can be orthogonal or perpendicular to the axis of the implant body and the lumen extending therethrough. Alternatively, the hole or window 160 can have any other angle (e.g., between 0 and 90 degrees, such as, for example, 0-5, 5-10, 10-15, 15-20, 20-25, 25-30, 30-35, 35-40, 40-45, 45-50, 50-55, 55-60, 60-65, 65-70, 70-75, 75-80, 80-85, 85-90 degrees, angles between the foregoing, etc.) relative to the lumen, as desired or required. As shown in FIG. 2A, the implant body 110 can include one or more ribs or other features or members 180 that extend at least partially (e.g., continuously or intermittently) along the length of the implant body 110 in a longitudinal direction. Such features or members 180 can help improve the rigidity of the implant body, prevent rotational movement of the implant body after implantation into a subject and/or provide one or more other benefits or advantages. In other embodiments, however, the implant body does not comprise such ribs or other external features. Instead, the implant body can comprise a polygonal cross-sectional shape (e.g., hexagonal, pentagonal, octagonal, square or other rectangular, triangular, etc.) along at least a portion of its length. Such a configuration can assist to prevent or reduce the likelihood that the implant will rotate or otherwise undesirably move or shift during or after implantation.

Figure 3:
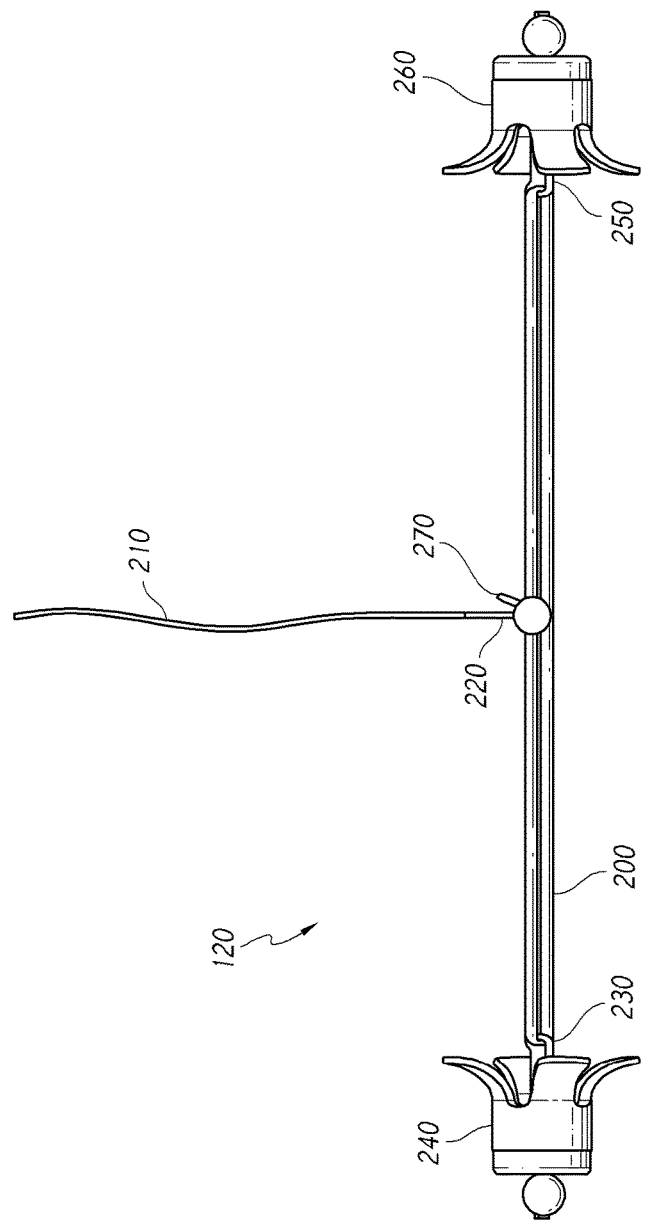
FIG. 3 illustrates a perspective side view of components of the tension assembly of the implant depicted in FIG. 2A.

FIG. 3 illustrates one embodiment of a tension assembly 120 that can be incorporated into a bone fusion implant, such as the one depicted in FIGS. 2A and 2B, 10, 12 or any other implant disclosed herein. In some embodiments, the tension assembly 120 comprises a suture loop 200 that includes one or more strands or ends of a suture tail 210. The suture tail 210 can pass through the suture side hole or window 160 of the implant body and form a sliding knot 220 which is held in at or near a junction of the body's inner lumen 130 and the suture side hole or window 160. In other embodiments, as disclosed herein with reference to the implant of FIG. 12, the suture system can include one or more knotless systems (e.g., located within a lumen of the implant body) to assist in providing and maintaining the necessary tension to the implant. Such a knotless design can be incorporated into any of the embodiments disclosed herein or variations thereof. In some embodiments, the outer dimension (e.g., outer diameter or other cross-section dimension) of the knot 220 is larger than the diameter or other cross-sectional dimension of the suture side hole or window 160 to ensure that the knot 220 remains within the lumen. In some embodiments, the side hole or window 160 and the inner lumen 130 are configured to retain the knot 220 in a fixed position relative to the implant body 110. In some embodiments, the suture side hole or window 160 is offset from a central axis of the implant body 110 to facilitate implantation.

According to some embodiments, as illustrated, for example, in FIG. 2A, the suture loop 200 extends from the knot 220 through the inner lumen 130 beyond the first end 140 of the implant body 110. The suture loop 200 can be looped through a first eyelet or other securement feature (e.g., loop, recess, etc.) 230 of a first bone anchor 240 back through the first end 140. In addition, the suture loop 200 can extend beyond the second end 150 to a second eyelet 250 of a second bone anchor 260. The suture loop 200 can terminate at a suture terminus 270 at or near the knot 220. In such an arrangement, as the suture tail 210 can be selectively pulled away from the implant body 110 to provide tension to the tension assembly 120 in order to bring the first and second bone anchors 240, 260 towards one another (e.g., in a direction of the implant body 110). In some embodiments, the suture system comprises two or more suture tails 210, as desired or required, to provide more robust control to the manipulation of the suture loop 200 and/or the bone anchors 240, 260 (and/or other bone engaging components) coupled thereto. In some embodiments, the knot 220 is configured so that when opposing forces are applied on the knot (e.g., in the longitudinal direction), the knot tightens to ensure that the first and second anchors 240, 260 travel towards the implant body 110. As discussed in greater detail herein, once radially deployed within corresponding bone bores, the bone anchors 240, 260 can be configured to affix to the corresponding bone bores (e.g., at least in one direction) to ensure that the tensile forces generated by the tension assembly 120 are maintained and that adjacent bones (e.g., across a joint) are moved into compressive contact with one another to promote fusion.

In some embodiments, the suture loop 200 is adjustable when the sliding knot 220 is held in a fixed position, for example within the inner lumen 130 adjacent to the suture side hole or window 140. As the suture tail 210 is tensioned or pulled away from the implant body 110, the tensile force between the bone anchors 240, 260 is increased. This can cause the distance between the bone anchors to be advantageously shortened. The size and shape of the orthopedic implant 100 can be modified, alternated or otherwise configured or re-configured according to a variety of applications or uses. For example, the implant 100 can be adapted for fusing bones in the hand or foot. Thus, the resulting implant may be smaller than an adaptation of the system for implantation in another portion of a subject's anatomy (e.g., wrist, cervical or other portion of a subject spine or neck). Accordingly, in some embodiments, the length, thickness, size, shape, other dimensions and/or other properties of the implant body 110, bone anchors 240, 260, tension assembly (e.g., suture loop) and the like can be adapted or customized according to a corresponding implant location and application.

Figure 4:
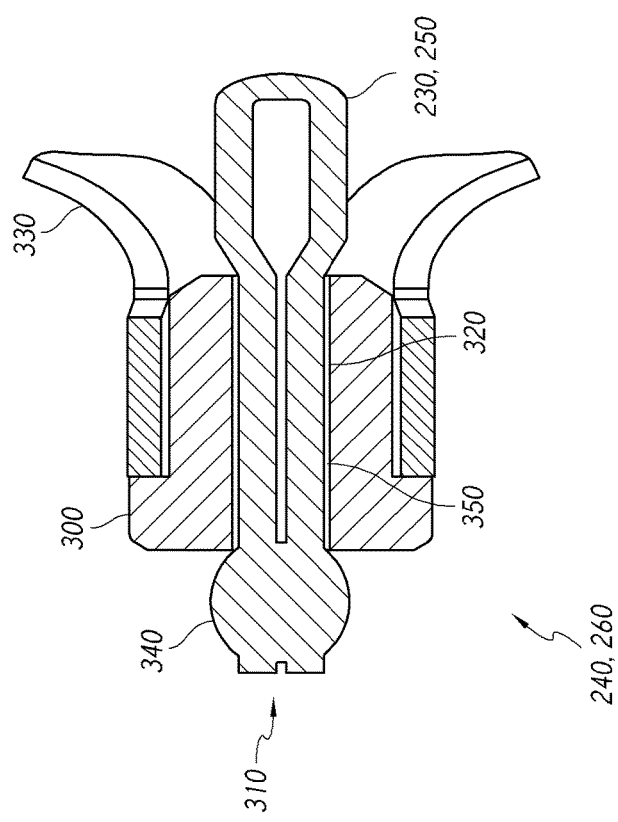
FIG. 4 illustrates a cross-sectional view of a bone anchor included the implant of FIG. 2A.

FIG. 4 illustrates one embodiment of a bone anchor 240, 260 that may be incorporated into an implant, such as those depicted in FIGS. 2A and 2B, 10 and 12A and/or any other configuration disclosed herein or variation thereof. As shown, the bone anchor 240, 260 can include an outer anchor tube 300 and an insert 310. In one embodiment, the anchor tube 300 defines a longitudinal channel 320 that is sized and/or otherwise configured to receive the insert 310. The anchor tube 300 can include a plurality of barbs, fingers or other engaging members 330 arranged radially at least partially about the anchor tube 300. Each barb or other engaging member 330 can extend from the anchor tube 300 outwardly and can be configured to engage bone at the implantation site for securing the bone anchor. In some embodiments, the barbs or other engaging members 330, once expanded, help form an interference or friction fit between the anchor and the adjacent bone surface. In some embodiments, the insert comprises one or more polymeric materials (e.g., PEEK), other rigid or semi-rigid materials (e.g. metals, alloys, etc.) and/or the like. Further, in some embodiments, the anchor tube 300 and one or more of its components (e.g., the barbs, fingers or other engaging members 330) comprise a shape memory materials (e.g., Nitinol), other metals or alloys, polymeric materials, other resilient materials and/or any other rigid, semi-rigid and/or flexible material, as desired or required.

With continued reference to FIG. 4, the insert 310 can include a head 340 and a shank 350 extending longitudinally from the head through the anchor tube 300. In some embodiments, an eyelet or other securement feature, element, member or device 230, 250 is positioned at or near the end of the shank 350 (e.g., opposite the head 340). The eyelet or securement element 230, 250 can advantageously permits the suture loop 200 to traverse through eyelet 230, 250 to secure the suture system to the anchor and to provide the necessary tension to the implant (e.g., as the suture tail 210 is tensioned by a surgeon or other practitioner). Other types of features or components configured to secure to the suture loop 200 can be used, either in lieu of or in addition to eyelets.

For any of the implant embodiments disclosed herein, including without limitation those depicted in FIGS. 2A and 2B, 10, 12A to 12C, etc., other types of bone anchors can be incorporated into the implant design, such as, for example, screw-in bone anchors with various thread arrangements, other types of interference or friction fit bone anchors and/or the like. Additional details regarding the bone anchors illustrated herein are provided in U.S. Patent Publication No. 2013/0211451, filed as U.S. patent application Ser. No. 13/673,626 on Nov. 9, 2012 and published on Aug. 15, 2013, the entirety of which is incorporated by reference herein and explicitly made a part of this specification.

According to some embodiments, during an arthrodesis or fusion procedure, portions of a pair of adjacent bones selected to be fused (e.g., the adjacent bones of a joint) are resected and a bore hole is drilled into each the adjacent bones such that the bores are substantially parallel and opposing each other when an implant is positioned therein. Thus, in some embodiments, it may be necessary to account for the amount of correction that is desired in a deformed joint in order to drill the bores in the adjacent bones. In some embodiments, in order to enhance the resulting fusion procedure, the adjacent bones are resurfaced at least partially along the surfaces against which the bones will contact one another. For example, a rasp or other bone removal device can be used to remove cartilage and/or bone tissue of one or both bones that will be fused. Holes or openings can be created in each of the bones so that the anchors, the implant body and other components or portions of the implant can be secured therein. Accordingly, the size of the holes, bores or other openings created in the bones can be carefully selected depending on the size of the implant to be used. In addition, the bores or other openings can be made large enough to accept a cannula or other delivery tools or instrumentation that will be used in the fusion procedure. According to any of the implantations and fusion methods and procedures disclosed herein, preparation of the targeted bone surfaces (e.g., decertification, drilling, etc.) can be performed, at least in part, using the tools and other devices disclosed in U.S. Provisional Patent No. 61/887,132, filed Oct. 4, 2013 and titled CIRCULATING BONE RASP, the entirety of which is hereby incorporated by reference herein and made a part of this specification.

In some embodiments, during insertion, the bone anchors 240, 260 are positioned within a cannula of a delivery system such that the barbs or other bone engaging members of the anchor are deflected radially inwardly (e.g., toward the longitudinal axis of the bone anchor 240, 260). The cannula can be withdrawn proximally to release the bone anchor 240, 260 therefrom. Once released from the cannula, the barbs or other engaging members of the bone anchor 240, 260 can self-expand radially outwardly to bear against and engage the adjacent bone tissue of the bore or opening. This helps secure the bone anchor 240, 260 therein. As discussed, for any of the embodiments disclosed herein or variations thereof, the barbs or other engaging members or portions of a bone anchor incorporated into an implant can comprise Nitinol and/or other shape memory materials that are configured to self-expand. In other configurations, one or more portions of a bone anchor can be actively expanded (e.g., using a radially expansion member). In some embodiments, the hole or bore is drilled deep enough into the target bone (e.g., phalanges of a subject's foot or hand, cervical vertebra, etc.) to accept the entire bone anchor 240, 260 and a portion of the implant body 110. However, as discussed in greater detail herein, the depth, diameter and/or other properties of the bone bores can be carefully selected and customized depending on the implant and corresponding fusion procedure implemented.

As discussed herein, the suture side hole or window 140 of the implant body 110 can be offset from the central axis of the implant body. In some embodiments, the bore hole that accepts the second bone anchor 260 can be longer or deeper to accept a greater portion of the implant body 110. Therefore, the bore hole which accepts the first bone anchor 140 can be relatively short or shallow, as it is configured to receive a shorter portion of the implant body 110. However, as described herein, the implant body 110 can be configured to be advantageously moved relative to the bore holes after initial placement in a subject. In this manner, for example, a greater portion or length of the implant body can be translated or moved into the distal bone to provide for more stable and reliable implantation across a joint. In some embodiments, the suture side hole 140 is positioned in the implant body 110 such that it coincides with an interface that is formed between the adjacent bones once they are pulled together. In other embodiments, the suture side hole or window 140 can be positioned within the distal and/or proximal bone bore or opening, as desired or required. The offset arrangement of the suture side hole 140 can facilitate implantation and reduce procedure time.

According to some embodiments, the first and second bone anchors 240, 260 and the implant body 110 are arranged in a cannula of a delivery tool in a pre-arranged manner, such that each of the bone anchor 240, 260 can be introduced into the corresponding bores or holes, either sequentially or simultaneously. Once the bone anchors, the implant body and/or any other components of the implant have been properly positioned with in the target bone bores, the cannula, delivery tools and/or other instrumentation can be withdrawn. As discussed in greater detail herein, the surgeon or other practitioner can manipulate the tension system (e.g., one or more tails or ends of a suture system) to properly position the implant within the subject and to create and maintain the necessary tension and resulting compressive forces between the adjacent bones to promote fusion. The ability to create and maintain tension in the suture system (and thus, to maintain compressive forces between adjacent bones) provides for enhanced and improved fusion of the bones. It also ensures that the surgeon or other practitioner can create and increase the necessary compression within the targeted joint after initial implantation of the implant body.

Figure 5:
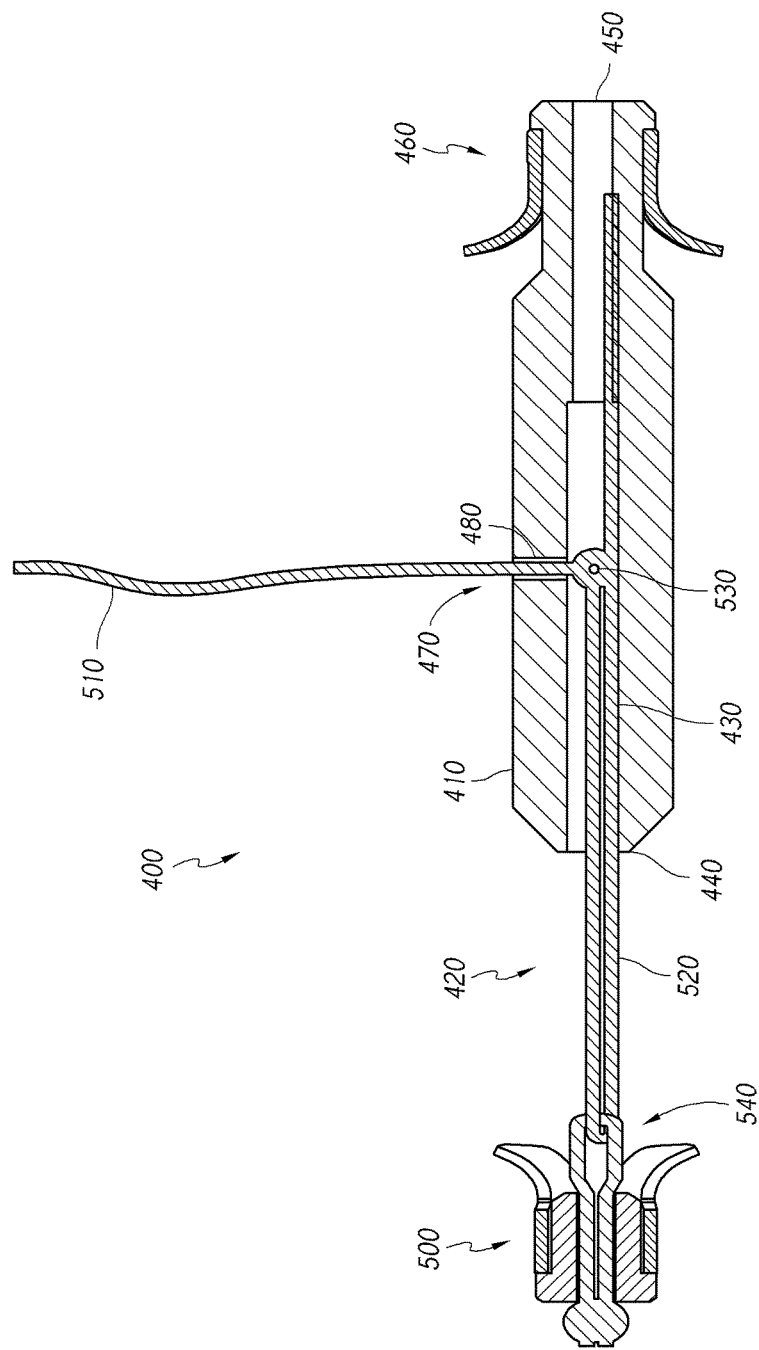
FIG. 5 illustrates a cross-sectional view of an orthopedic repair implant according to another embodiment.

With reference to FIG. 5, another embodiment of an implant 400 is illustrated. As with the system depicted in FIG. 2A, the implant 400 can include an implant body 410 and a tension assembly 420. In some embodiments, the implant body 410 comprises a rigid, semi-rigid and/or flexible structure that defines one or more inner lumens 430 that extend longitudinally through the implant body 410. As with other implant body configurations disclosed herein, the implant body 410 can include a polygonal (e.g., hexagonal, octagonal, pentagonal, etc.) cross-sectional shape. However, the implant body 410 can include any other cross-sectional shape, such as, for example, square, rectangular, triangular, circular, oval, irregular and/or the like, as desired or required. As shown, the implant 400 can include one or more anchors at either end to help secure the system to a subject's bone tissue. In addition, in some embodiments, the implant body 410 comprises a suture side hole or window 470 that extends from the inner lumen 430 to the exterior of the implant body 410, thereby allowing external access to the inner lumen 430.

Figure 6:
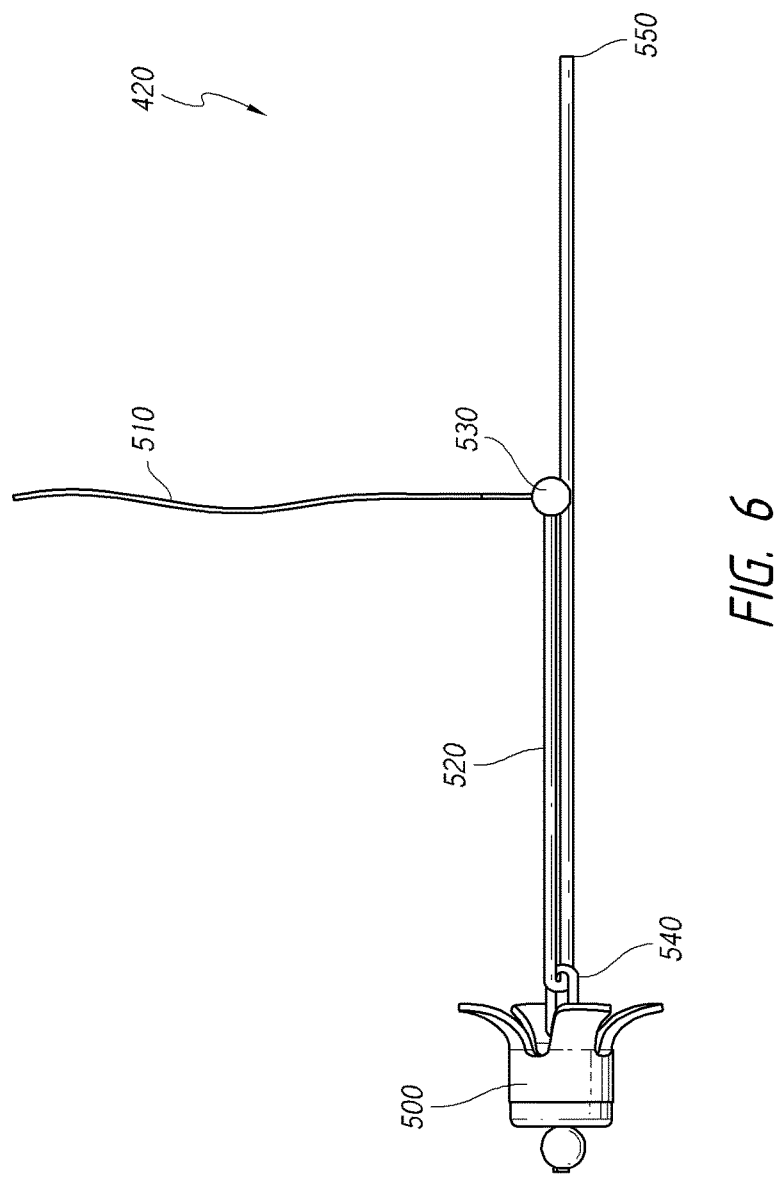
FIG. 6 illustrates a perspective side view of components of the tension assembly of the implant depicted in FIG. 5.
Figure 7:
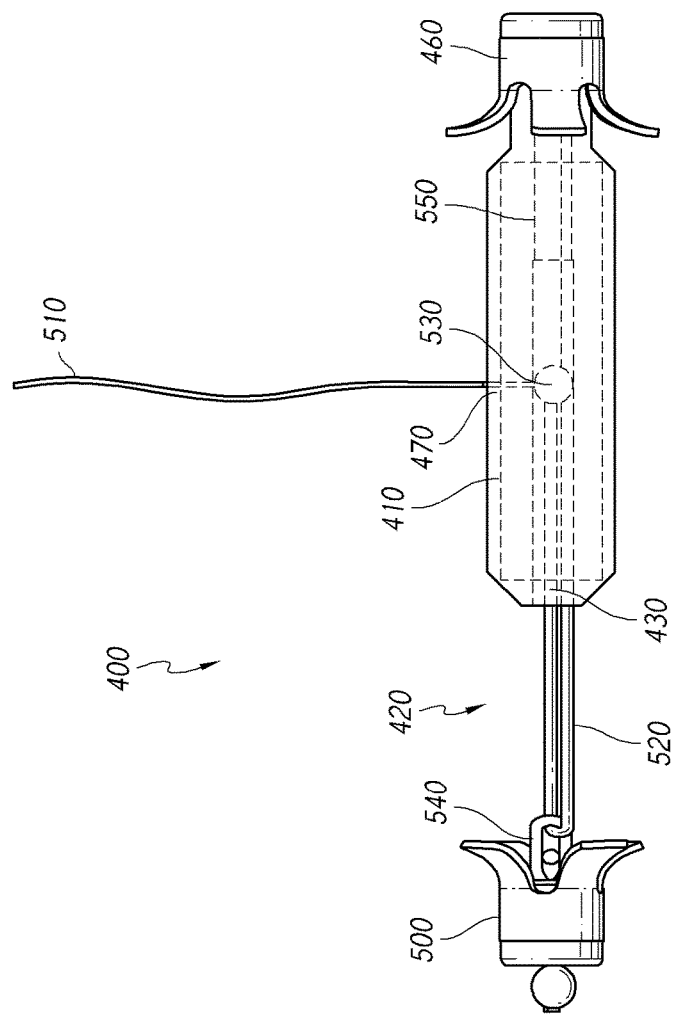
FIG. 7 illustrates a perspective view of the implant of FIG. 5.

FIG. 6 illustrates one embodiment of a tension assembly 420 that can be incorporated into the implant of FIG. 5 or any other implant disclosed herein. In the depicted embodiment, the tension assembly 420 includes one bone anchor 500 that is separate from the implant body 410. As shown in FIGS. 5 and 7, a second bone anchor 460 is integrated into the implant body 410, thereby forming a unitary structure with the implant body. In some embodiments, the implant body 410 and the second bone anchor 460 can be releasably or permanently secured to one another, as desired or required. Similar to other embodiments disclosed herein, a tail or free end 510 of a suture loop 520 can be configured to pass through a side hole or window 470 of the implant body 410. In some embodiments, the hole or window 470 is sized, shaped and otherwise adapted to secure a knot 530 (e.g., a sliding knot) of the suture system in place within the inner lumen 430 of the implant body 410.

With continued reference to FIGS. 5-7, a suture loop 520 can extend from the knot 530 through the inner lumen 430 of the implant body. Since the opposing bone anchor 460 is integrated into the implant body 410, the suture loop 420 may not pass through a second eyelet. Rather, in some embodiments, the suture loop passes through only a single eyelet or securement element 540 (e.g., the eyelet or securement element of a first bone anchor 500) and is fixedly terminated within the implant body 410 at the suture terminus 550. The sliding knot 530 can be formed such that when opposing forces are applied on the sliding knot 530 (e.g., in the longitudinal direction), the first bone anchor 500 is moved closer to the implant body and the integrated anchor and the knot tightens to ensure that the anchor 500 and the implant body 410 remain fixed relative to one another.

Unlike other configurations disclosed herein that include two bone anchors 240, 260 that are physically separated from the implant body 110, the implant 400 embodiment illustrated in FIGS. 5-7 includes a single independent bone anchor 500 and a bone anchor 460 which is integrated into the implant body 410. In some embodiments, such an arrangement can reduce the complexity of the implant 400, improves a rigidity and robustness of a planned orthopedic fusion and/or provide one or more additional benefits or advantages. In other embodiments, however, it may be preferred or desired to include separate anchors, based on the particular application or use of the implant.

Figure 8:
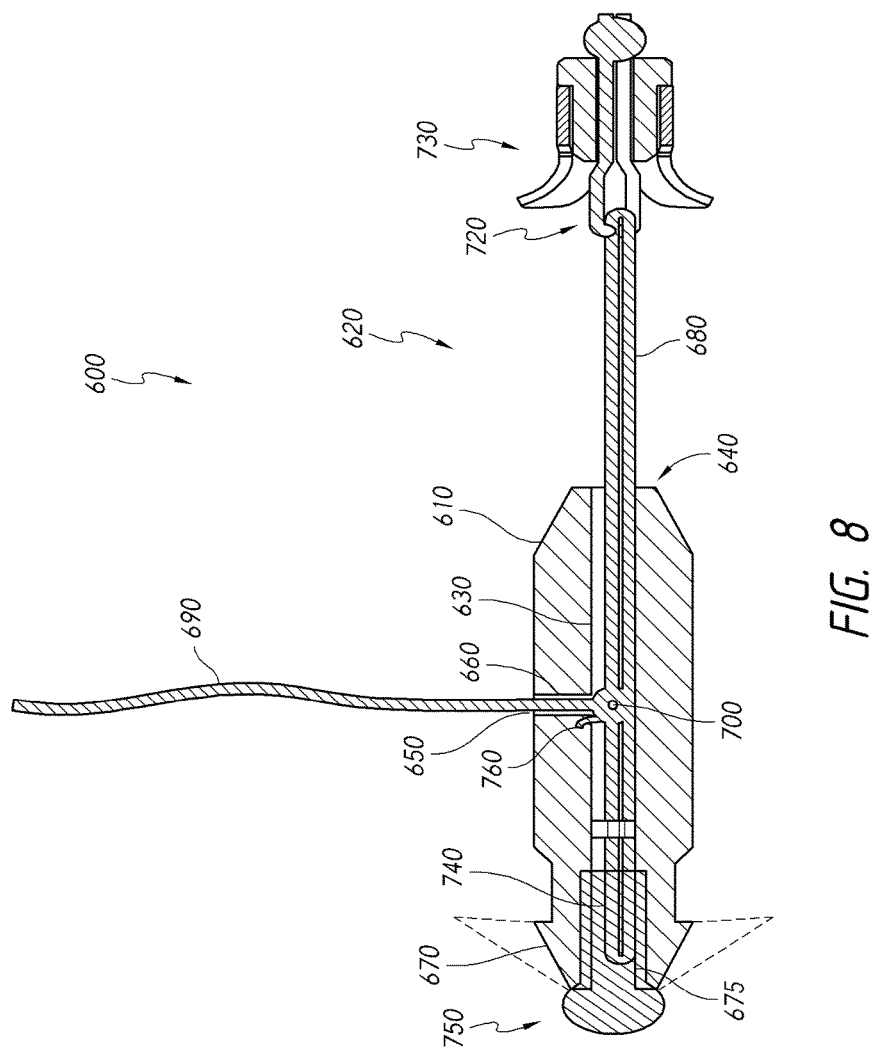
FIG. 8 illustrates a cross-sectional view of an orthopedic repair implant according to another embodiment.
Figure 9:
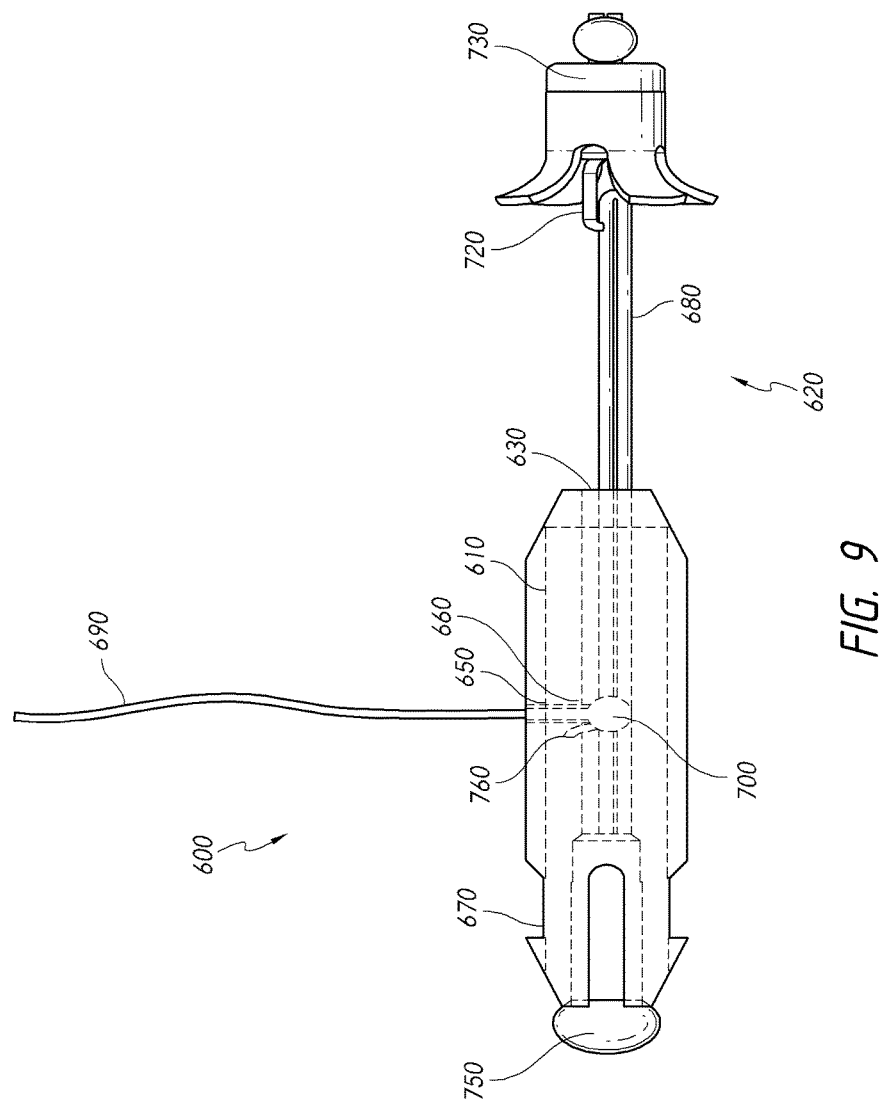
FIG. 9 illustrates a perspective side view of the implant depicted in FIG. 8.

FIGS. 8 and 9 illustrate another embodiment of an implant 600 that can be used to treat hammer toe or another orthopedic deformity or condition of a subject. As shown, the implant 600 can comprise an implant body 610 and a tension assembly 620. The implant body 610 can include a rigid, semi-rigid and/or flexible structure that can have a generally tubular shape. In some embodiments, the cross-sectional shape of the implant body 610 can be polygonal (e.g., hexagonal, octagonal, pentagonal, square or rectangular, triangular, etc.), circular or oval, irregular and/or any other shape, as desired or required. As disclosed herein with reference to other embodiments, the depicted implant body 610 can include one or more lumens 630 that extend longitudinally through it (e.g., along the central or major axis of the implant body 410, along another, non-central axis, etc.) to form at least one open end 640. Further, the implant body 610 can include a side hole or window 650 that extends from the inner lumen 630 to the exterior of the implant body 610 and that provides access to the inner lumen 630 from the exterior of the implant body 610.

With continued reference to the cross-sectional view of FIG. 8, one end of the implant body 610 can include an expandable element 670 that is configured to be selectively radially expanded to help anchor the implant body 610 within a bore or hole of a targeted bone. As shown, the expandable element 670 can include a longitudinal channel 675 that is configured to receive an expanding insert. In some embodiments, such an insert can be larger in diameter or other cross-sectional dimension than the longitudinal channel 675. Accordingly, when the expanding insert is pulled into the longitudinal channel, the expanding element 670 is forced at least partially radially outwardly (e.g., as depicted schematically by the dashed lines in FIG. 8) to engage, at least partially, the inner wall of the bone bore or opening hole into which it is positioned. Thus, the expandable element 670 can help create an interference or friction fit between the implant body 610 and the adjacent bone tissue. As noted herein with reference to the embodiment depicted in FIGS. 5-7, such a configuration can replace one of the separate bone anchors, and instead, integrate a similar one engaging member or feature into the implant body itself. Such a design can be incorporated into any of the implant embodiments disclosed herein, including, without limitation, the implants of FIG. 10 or 12A-12C.

As illustrated in FIGS. 8 and 9, the tension assembly 620 can comprise a suture loop 680 having a suture tail or free end 690 that passes through the suture side hole or window 650. As with other embodiments disclosed herein, the depicted suture loop can be configured to form a knot 700 (e.g., sliding knot) that is held in place within the inner lumen 430 adjacent to the side hole or window 650. The suture loop 680 can extend from the knot 700 through the inner lumen 630 and beyond an open end 640 of the implant body 610. The suture loop 680 can be looped through an eyelet or other securement element or feature 720 of a bone anchor 730 and back through the open end 640. In some embodiments, the loop 680 extends and is secured to the anchor that is integrated with the implant body 610 (e.g., along an opposite end of the body 610). The suture loop 680 can terminate at a suture terminus at or near the knot 700. As discussed above, a wedge or other insert 750 located at or near the integrated bone anchor 670 can be used as an expanding insert to at least partially force the expanding element 670 radially outwardly so that at least a portion of the anchor 670 engages and secures to adjacent bone tissue of a subject. In some embodiments, the knot 700 is formed such that when opposing forces are applied on the knot 700 (e.g., in the longitudinal direction), the knot tightens to ensure that the bone anchors or other bone engaging components or features of the implant 730, 670 remain fixed relative to one another.

With continued reference to FIGS. 8 and 9, in some embodiments, as the suture tail 690 is tensioned or pulled away from the implant body 610, the suture loop 680 forces the separate bone anchor 730 towards the open end 640 of the implant body 630 and pulls the wedge or other expanding insert 750 into the longitudinal channel 675 (e.g., causing the expanding element 760 to at least partially radially expand outwardly). In some embodiments, e.g., such as those illustrated in FIGS. 5-9, since a bone anchor or other bone engaging feature is integrated into the implant body, the entire implant body forms an interference or friction fit with the bore or hole of the targeted bone structure.

Figure 10:
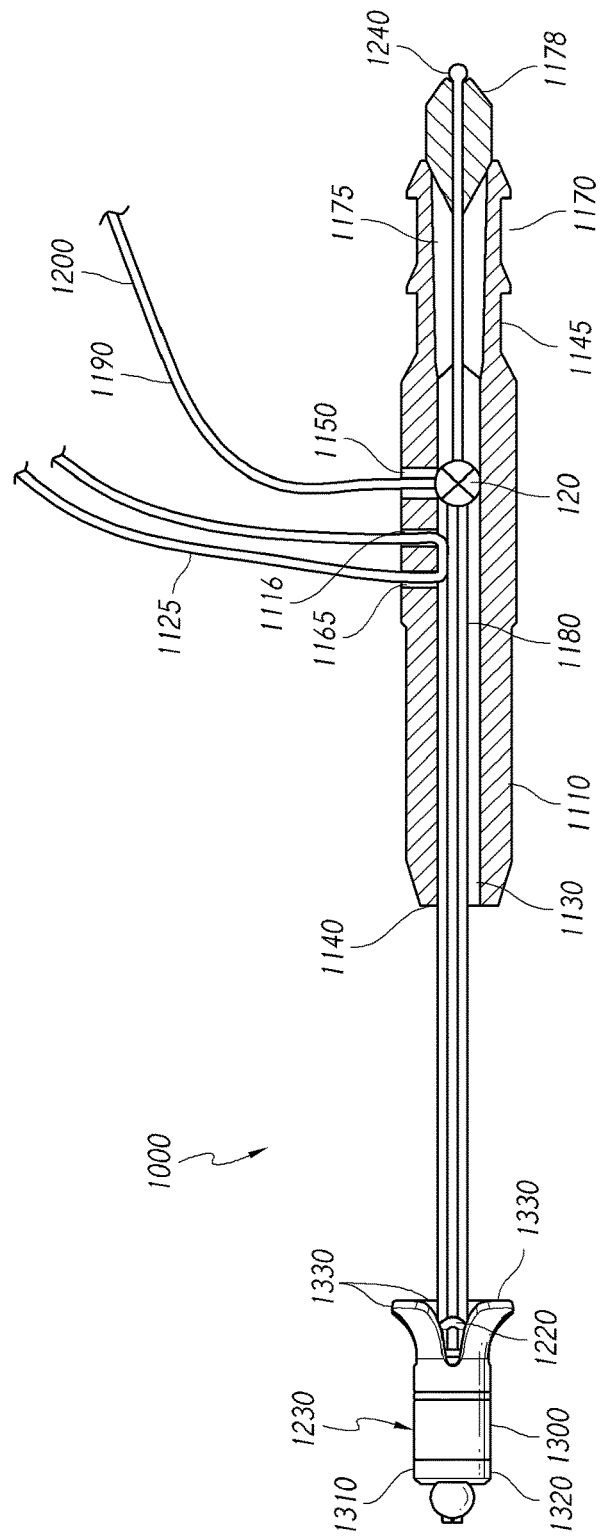
FIG. 10 illustrates a partial cross-sectional view of one embodiment of an orthopedic repair implant.

FIG. 10 illustrates a cross-sectional view of another embodiment of an implant 1000 used to treat hammer toe and/or another orthopedic deformity or condition. As shown, the implant 1000 can include an implant body 1110 and a tension assembly 1120 at least partially routed therethrough. As with other embodiments disclosed herein, the tension assembly 1120 can comprise one or more bone anchors or other bone engaging components or elements. The bone anchors or other bone engaging elements or components can be separate from or integrated with the implant body 1110, as desired or required. In some embodiments, the implant 1000 can further include a positioning element 1125 that is used to selectively move (e.g., translate along the longitudinal axis of the implant body 1110) the implant body 1110. As discussed in greater detail herein, such movement of the implant body can occur after initial positioning of the implant body within the corresponding bone bores or openings.

According to some embodiments, the implant body 1110 can include a rigid, semi-rigid and/or flexible structure having a polygonal (e.g., hexagonal, square, other rectangular, triangular, pentagonal, octagonal, etc.) cross-sectional shape. In other embodiments, the implant body 1110 can include a different cross-sectional shape, such as, for example, circular, oval, square, rectangular, triangular, other polygonal, irregular and/or the like. In some embodiments, the use of an implant body 1110 having a polygonal shape helps ensure that the implant body will not rotate or otherwise move undesirably after completion of an implantation procedure. For example, the corners formed by the polygonal shape can provide for improved engagement with adjacent bone surfaces to reduce the likelihood of rotation or other movement when the implant is subject to various forces or moments post-implantation.

With continued reference to FIG. 10, the implant body 1110 can comprise an inner lumen 1130 that extends along a longitudinal axis of the implant body 1110 from its open proximal end 1140 to its distal end 1145. In other embodiments, the inner lumen 1110 extends only partially within the implant body 1110. In addition, the implant body can include more than one lumen (e.g., 2, 3, 4 lumens, more than 4 lumens, etc.), as desired or required.

With continued reference to FIG. 10, the implant body 1110 can include a suture side hole or window 1150 that extends from the inner lumen 1130 to the exterior of the implant body 1110. Although the implant body 1110 illustrated herein is shown as generally straight, in other embodiments, the implant body 1110 may be formed with a bend having a desired angle. In some embodiments, the angle can vary between 0 and 30 degrees (e.g., 0, 1, 2, 3, 4, 5, 6, 7, 8, 9, 10, 11, 12, 13, 14, 15, 16, 17, 19, 20, 21, 22, 23, 24, 25, 26, 27, 28, 29, 30 degrees, values between the foregoing angle ranges, etc.), greater than 30 degrees (e.g., 30-40, 40-50, 50-60 degrees, greater than 60 degrees, etc.), etc. In some embodiments, such a bend or angle in the implant body 1110 can approximate the natural angle of the phalangeal bones adjacent the targeted joint (e.g., the proximal and intermediate phalanges of a subject's foot, other phalangeal bones of a subject's foot or hand, etc.). Such a bend can help position the subject's toes, fingers or other bones in a more proper alignment and orientation following implantation of an implant. In some embodiments, the implant comprises two or more bends or angles. In other embodiments, the implant body comprises a non-linear shape along one or more portions. For example, one or more sections of the implant body can include a rounded or curved shape, a sinusoidal shape, an irregular shape and/or the like.

In some embodiments, the implant body 1110 comprises one or more rigid, semi-rigid and/or flexible materials. For example, the implant body 1110 can include one or more polymers, metals (e.g., stainless steel), alloys, other biocompatible, bioresorbable and/or osteoinductive materials, radiolucent materials, elastomeric materials and/or any other material. In some embodiments, the implant body 1110 comprises polyether ether ketone (PEEK), polyphenylene, polysulfone, polyethylene, or other suitable polymeric materials.

According to some embodiments, the implant body 1110 can include one or more longitudinal projections or ribs (e.g., extending along an exterior of main implant body) that operate to enhance bone engagement, help resist rotational movement of the implant body 1110 in situ and/or provide additional advantages and benefits to the implant. Such ribs or projections can extend continuously or intermittently along the length of the implant body. Further, the ribs or projections can extend along certain circumferential locations of the implant body (e.g., along every 30, 45, 60, 90, 180 degrees, angles between the foregoing values, etc.). The ribs or projections 1110 can include any shape, size and configuration. For example, in some embodiments, the projections include a generally rectangular shape when viewed from the side, such that the distance by which the projection extends from the exterior surface of the main portion of the implant body is constant or generally constant along the length of the implant body. In other embodiments, however, the ribs or other projections can include a different shape (e.g., circular or oval, curved, fluted, sinusoidal, triangular, other polygonal, stepped, irregular, etc.). Thus, is some configurations, the peripheral extent of a rib or projection relative to the exterior surface of the main portion of the implant body (e.g., when viewed from a cross-section generally perpendicular to the longitudinal axis of the implant body) varies along the length of the rib or projection. Such ribs or projections can include one or more sharp surfaces or edges to provide enhanced engagement with adjacent bone tissue. In some embodiments, the radial extension distance of the ribs or projections is between 0 and 3 mm (e.g., 0-0.5, 0.5-1, 1-1.5, 1.5-2, 2-2.5, 2.5-3 mm, lengths between the foregoing values, more than 3 mm, etc.). In some embodiments, the radial extension distance of the ribs or projections is between 0 and 100% of the diameter or cross-sectional dimension of the main portion of the implant body (e.g., 0-5, 5-10, 10-20, 20-30, 30-40, 40-50, 50-60, 60-70, 70-80, 80-90, 90-100, 100-120, 120-140, 140-160, 160-180, 180-200%, percentages between the foregoing values, greater than 200%, etc.). Such ribs or other projections can be incorporated into any of the implant body designs disclosed herein or variations thereof. As noted herein, alternatively or in addition to such ribs or projections, the implant body can include a polygonal cross-sectional shape (e.g., hexagonal) that helps prevent the likelihood of rotation of the implant body post implantation.

With continued reference to FIG. 10, a pair of through-holes or openings 1165, 1166 can extend through the implant body 1110 to the inner lumen 1130. A positioning element 1125, which in the illustrated embodiment comprises a loop of suture material, can extend through the through-holes 1165, 1166 and can be accessible by a surgeon or other practitioner outside the implant body 1110. As discussed in greater detail herein, the positioning element 1125 can be used to adjust the position of the implant body 1110 relative to the bone structures during an implantation procedure, thereby facilitating the ease of implantation, enhancing the degree of stabilization provided by the implant 1000 to the corresponding bone structures and/or providing one or more other benefits and advantages. For example, the positioning element 1125 and the corresponding features of the implant body 1110 (e.g., the openings 1165, 1166 of the implant body 1110) can be used to advance the implant body deeper into a distal bore or opening after initial positioning. In some embodiments, the surgeon can manipulate the positioning element 1125 to apply a force in a desired direction. Thus, for example, the implant body (and, in some embodiments, an adjacent bone anchor) can be advantageously advanced, shifted or otherwise moved deeper into a corresponding bone bore (e.g., distal or proximal).

In the embodiment illustrated in FIG. 10, the positioning element 1125 comprises a suture loop extending through the through-holes 1165, 1166 to couple the positioning element 1125 to the implant body 1110. However, in other embodiments, the positioning element 1125 includes a different configuration or method of attachment to the implant body 1110, as desired or required. For example, in some embodiments, the positioning element 1125 can include one or more tabs, openings, other projections or recesses, other features or components, combinations of the foregoing and/or the like positioned along a portion of the implant body that can be used to move the implant body after the implant body has been initially positioned within one or more bone bores of a subject.

In some embodiments, the positioning element 1125 can include any flexible structure having the physical properties (e.g., tensile strength, durability, etc.) sufficient to overcome tensile forces applied by the surgeon to it to transfer such forces to the implant body in order to adjust the position of the implant 1000 during the particular procedure. In addition, in lieu of the through-holes or openings 1165, 1166 included in the illustrated embodiment, in other embodiments, the positioning element 125 can be attached to the implant body 1110 by other devices, techniques or methods, such as, for example, adhesives, mechanical fasteners, friction or interference fit connections, knots, pledgets and/or the like. Furthermore, while in the illustrated embodiment the implant 1000 includes a separate tension assembly 1120 and positioning element 1125, in other embodiments, the functionality of these components can be provided in a single suture assembly. For example, the tension system of FIGS. 12A-12C can be used both to create tension between the opposing bone anchors and to shift (or translate) the implant body relative to the distal and/or proximal bores after initial placement of the implant therein.

In the embodiment illustrated in FIG. 10, an expandable element 1170 is positioned along a distal end 1145 of the implant body 1110. The expandable element 1170, when at least partially radially expanded, can be used to engage the expandable element 1170 to adjacent bone tissue, and thereby, anchor the implant body 1110 within a targeted bore or opening. In some embodiments, the expandable element 1170 includes a longitudinal channel 1175 (e.g., along one or more interior portions) that is configured to at least partially accept a wedge or other insert 1178 therein. In some embodiments, such an insert or wedge include an outer diameter or cross-sectional dimension that is larger than the diameter or other cross-sectional dimension of the longitudinal channel 1175. Accordingly, in some embodiments, when the insert or wedge 1178 is pulled into the longitudinal channel, at least a portion of the expandable element 1170 deflects radially outwardly to engage adjacent bone tissue of the corresponding bore in which it is positioned. Thus, in some configurations, an interference or friction fit is created between the implant body 1110 and the bone itself upon radial expansion of the expandable element 1170 of the implant body 1110. Such a configuration can be incorporated into any of the implant embodiments disclosed herein or variations thereof.

Figure 18:
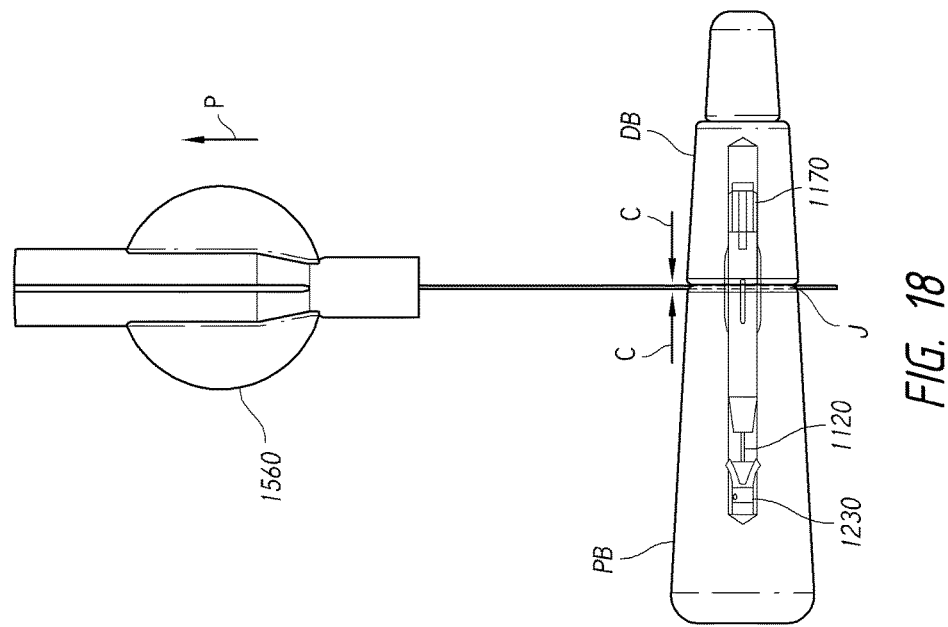

As discussed in greater detail herein with reference to FIGS. 2A and 18, in other embodiments, an implant can include bone anchors (and/or other bone engaging members or components) that are separate and distinct from the implant body 1110. A positioning assembly can be incorporated into any of the implant embodiments disclosed herein or variations thereof. As discussed above, such a positioning assembly can include through-holes or openings through which a suture loop (or other flexible member) can be positioned. Alternatively, the positioning assembly can include a different configuration that enables a surgeon or other practitioner to selectively move the implant body of the implant after initial positioning within a target anatomical location (e.g., within opposing bores on either side of a joint, fracture, etc.).

With continued reference to FIG. 10, as with other embodiments disclosed herein, the tension assembly 1120 can comprise a suture loop 1180 having one or more suture tails or free ends 1190 that pass through a suture side-hole or window 1150 of the implant body 1110 and help form a sliding knot 1200, knotless suture system and/or the like therein. In some embodiments, the knot 1200 is securely held in place within the inner lumen 1130 of the implant body 1110 adjacent to suture side hole or window 1150, such that the position of the knot 1200 does not move during use.

As discussed in greater detail herein, the knot can be sized, shaped and otherwise configured to be retained within the lumen of the implant body 1110 during use. For example, the diameter or cross-sectional dimension of the knot can be larger than the diameter or cross-sectional dimension of the side-hole or window 1150 so that the knot cannot exit the lumen of the implant body. In some embodiments, the diameter or cross-sectional dimension of the knot is approximately 0 to 30% (e.g., 1, 2, 3, 4, 5, 5-10, 10-15, 15-20, 20-25, 25-30%, percentages between the foregoing values, less than 1%, etc.) larger or more than 30% larger (e.g., 30-40, 40-50, more than 50%, etc.) than the diameter or cross-sectional dimension of the side-hole or window 1150.

As shown in FIG. 10, the suture loop 1180 can extend from the formed knot 1200 through the inner lumen 1130. In some arrangements, the suture loop 1180 is routed beyond the open end 1140 of the implant body 1110, positioned through an eyelet or other securement feature 1220 of a bone anchor 1230 and back through the open end 1140. The suture loop 1180 can continue through the inner lumen 1130 of the implant body 1110 and through an eyelet or other securement feature 1240 of the wedge or insert 1178. In some embodiments, the wedge or insert 1178 is configured to force the expandable element 1170 radially or laterally outwardly when moved into an interior portion of the expandable element 1170. This can cause the expandable element 1170 to at least partially engage adjacent bone of the target bore or hole in which the implant body 1110 is positioned. According to some arrangements, the knot 1200 is designed and configured such that when opposing forces are applied on the knot 1200 in the longitudinal direction (e.g., by selectively manipulating the suture tails or free ends 1190 of the suture assembly 1120), the knot tightens to apply and maintain tension between the bone anchor 1230 and the expandable element 1170 along the opposite end of the implant. As discussed herein with reference to FIGS. 2A and 12A-12C, the expandable element 1170 or other bone engaging portion that is integrated into the structure of the implant body 1110 can be separate and distinct from the implant body 1110. Accordingly, in some embodiments, two separate an opposing bone anchors can be used on either side of an implant body 1110.

According to some embodiments, as the suture tail or free end 1190 is tensioned or pulled away from the implant body 1110, the suture loop 1180 is tightened, thereby urging the bone anchor 1230 toward the open end 1140 of the implant body 1110. In some arrangements, manipulation of one or more of the tails or free ends of the suture loop 1180 can also radially expand or otherwise deploy the expandable element 1170 (or, in other configurations, a second bone anchor). For example, manipulation of a tail or free end of the suture loop can advance the wedge or insert 1250 at least partially into the longitudinal channel 1175 of the expandable element. Accordingly, the expandable element 1170 can be urged at least partially radially outwardly to engage bone tissue and secure the anchor within the corresponding bone bore. In some embodiments, a single tail or free end of the suture loop is manipulated to radially expand an expandable element 1170 (or other bone anchor) and to simultaneously apply tension between bone anchoring elements positioned on opposite ends of the implant (e.g., bone anchors, expandable elements, etc.). Alternatively, however, the suture loop 1180, the knot and/or other components of the tension assembly 1120 can be designed and otherwise configured to separately or individually deploy one or more anchoring members (e.g. anchors, expandable elements, etc.) and to apply tension to the implant.

As noted herein, according to some embodiments, such as the implant 1000 of FIG. 10, at least one bone anchor or bone engaging element 1170 is integrated into the implant body 1110. Thus, under such a configuration, the implant body 1110 can form an interference or friction fit with the bore hole within the selected bone, at least along the location of the implant body that includes the expandable element or other bone engaging features. Such embodiments can reduce the complexity of the implant, improve the rigidity and robustness of an orthopedic fusion procedure and/or provide additional benefits and advantages.

With continued reference to FIG. 10, the bone anchor 1230 can include an outer anchor tube 1300 and an insert 1310 disposed partially within the anchor tube 1300. The insert 1310 can include a head portion 1320 that contacts and bears upon an end of the anchor tube 1300. In some embodiments, the anchor tube 1300 includes a plurality of deflectable fingers or other engaging members 1330 that are configured to be deflectable radially inwardly when advanced through a delivery cannula and/or bone bore. Such fingers or engaging members 1330 can be biased radially outwardly when properly positioned within a bone bore, such that they can engage a surface of the bore to secure the bone anchor 1230 thereto. The eyelet or other securement member 1220 of the bone anchor can be coupled to the head portion 1320 of the insert 1310, such that when tension is applied to the eyelet or other securement member 1220 (e.g., via pulling of the suture loop 1180 that is attached to the eyelet or other securement member), such a tensile force is transmitted to the head portion 1320 and adjacent portions of the anchor.

In some embodiments, once an anchor 1230 is delivered and deployed within a bone bore and its fingers or engaging members assume a radially expanded orientation (e.g., as illustrated in FIG. 10), movement of the anchor 1230 in the direction of the implant body 1110 is prevented or limited. This can be due, at least in part, on the orientation of the fingers or bone engaging members 1330 relative to the direction of tension applied to the anchor. In some embodiments, the anchor comprises one or more biocompatible rigid, semi-rigid and/or flexible materials that provide the desired structural characteristics (e.g., strength, durability, flexibility, longevity, etc.) to the overall implant design. For example, in some embodiments, the insert 1310 of the anchor and/or the anchor tube 1300, including the deployable fingers or other engaging members extending therefrom, can include one or more polymeric materials (e.g., polyether ether ketone or PEEK, polyphenylene, polysulfone, polyethylene, etc.). In other embodiments, at least one or more of the components of the bone anchor 1230 comprise other materials, either in lieu of or in addition to suitable polymeric materials, that provide the desired properties to the anchor, such as, for example, metals or metal alloys (e.g., stainless steel, Nitinol or other shape memory materials, etc.), elastomeric materials (e.g., biocompatible rubbers) and/or the like. According to one embodiment, the insert 1310 of the anchor comprises PEEK and/or other polymeric materials, while the anchor tube 1300 comprises Nitinol, another shape memory material and/or another metal or alloy configured to at least partially radially expand (e.g., self-expand, with the assistance of a separate member, etc.) to engage adjacent bone tissue.

Additional details regarding the bone anchors illustrated herein are provided in U.S. Patent Publication No. 2013/0211451, filed as U.S. patent application Ser. No. 13/673,626 on Nov. 9, 2012 and published on Aug. 15, 2013, the entirety of which is incorporated by reference herein and explicitly made a part of this specification. In other embodiments, other bone anchor configurations can be employed. The bone anchor 1230 can include any configuration suitable to permit the bone anchor 1230 to be inserted into a bone bore, and to thereafter engage the bone bore surface so as to resist being pulled from the bone bore in the direction opposite the insertion direction (e.g., in the direction of the implant body). Such anchors (e.g., those discussed with reference to FIG. 10) can be incorporated into implant disclosed herein, such as, for example, without limitation, the implant of FIGS. 12A-12C.

Figure 11:
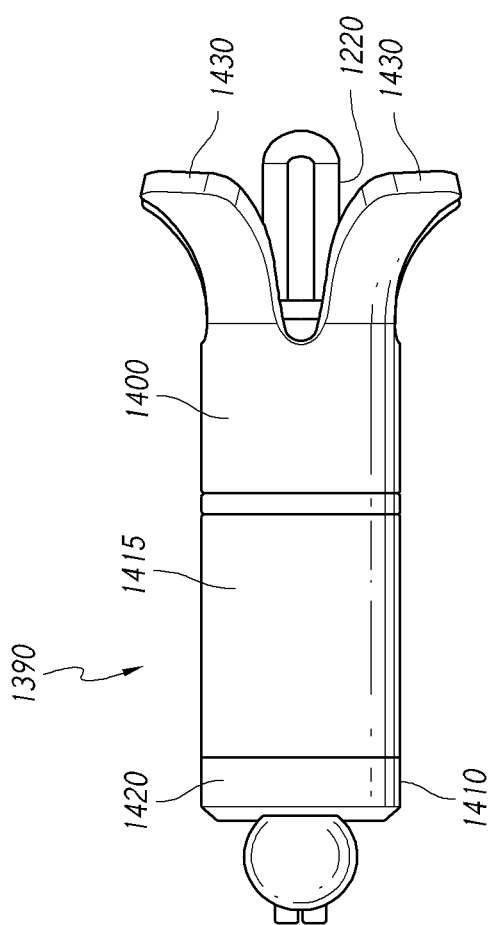
FIG. 11 illustrates one embodiment of a bone anchor that can be incorporated into the implant depicted in FIG. 10.

FIG. 11 illustrates a side view of an alternative embodiment of a bone anchor 1390 that can be used in the implant 1000 in lieu of the bone anchor 1230 (or in any other implant design disclosed herein). As shown, the bone anchor 1390 includes an outer anchor tube 1400, an insert 1410, and an elastic member or portion 1415. The insert 1410 can include a head portion 1420 and the anchor tube 1400 that comprises a plurality of deflectable fingers or engaging members 1430 for contacting and engaging the bone surface of a bone bore when inserted and positioned therein. In addition, an eyelet or other securement feature 1220 can be secured to or incorporated into the head portion 1420.

With continued reference to FIG. 11, the bone anchor 1390 can comprise one or more elastic members 1415 to provide for a variable compressive force to the anchor tube 1400 when a tensile force is applied to the insert 1410 (e.g., via a suture loop mechanically coupled thereto). As shown, the elastic member 1415 can comprise a tube or other structure positioned between the head portion 1420 of the insert 1410 and an end 1440 of the anchor tube 1400. Thus, in some embodiments, when the fingers or other deployable members 1430 engage an adjacent bone surface and tension is applied to the eyelet or other securement feature 1220, the head portion 1420 of the insert 1410 can abut and bear upon the elastic member 1415. In turn, the elastic member can bear upon the end 1425 of the anchor tube 1400. In some embodiments, the elastic member 1415 comprises one or more elastic or semi-elastic materials, such as, for example, rubbers, other elastomers, polymeric materials, resilient metals and/or alloys, other resilient or compressible materials and/or the like. Accordingly, in such configurations, a variable compressive force can be applied to the anchor tube 1400 in response to a tensile force on the eyelet or other securement feature 1220. In addition, the elastic member 1415 can operate similar to a compression spring, such that it maintains a compressive force on the anchor tube 1400, even as tension in the eyelet or other securement feature 1220 is relaxed or eased. According to some embodiments, the elastic element 1415 can comprise a variety of biocompatible, elastomeric and/or other materials, such as, without limitation, silicone rubbers, polyisoprene, other elastomeric and/or resilient materials and/or the like. Such anchors (e.g., those discussed with reference to FIG. 11) can be incorporated into implant disclosed herein, such as, for example, without limitation, the implant of FIGS. 12A-12C.

Figure 12A:
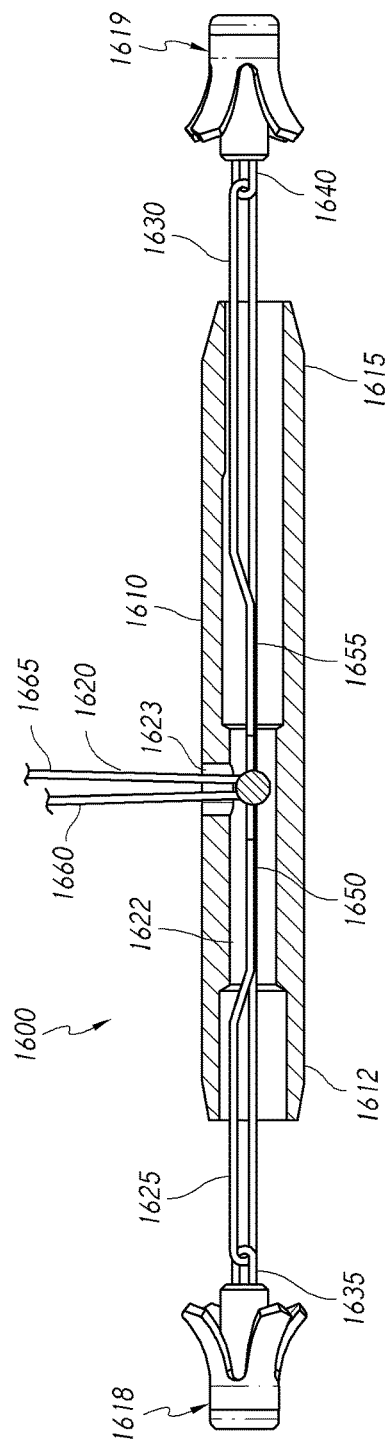
FIGS. 12A and 12B illustrate different views of an orthopedic repair implant according to another embodiment.
Figure 12B:
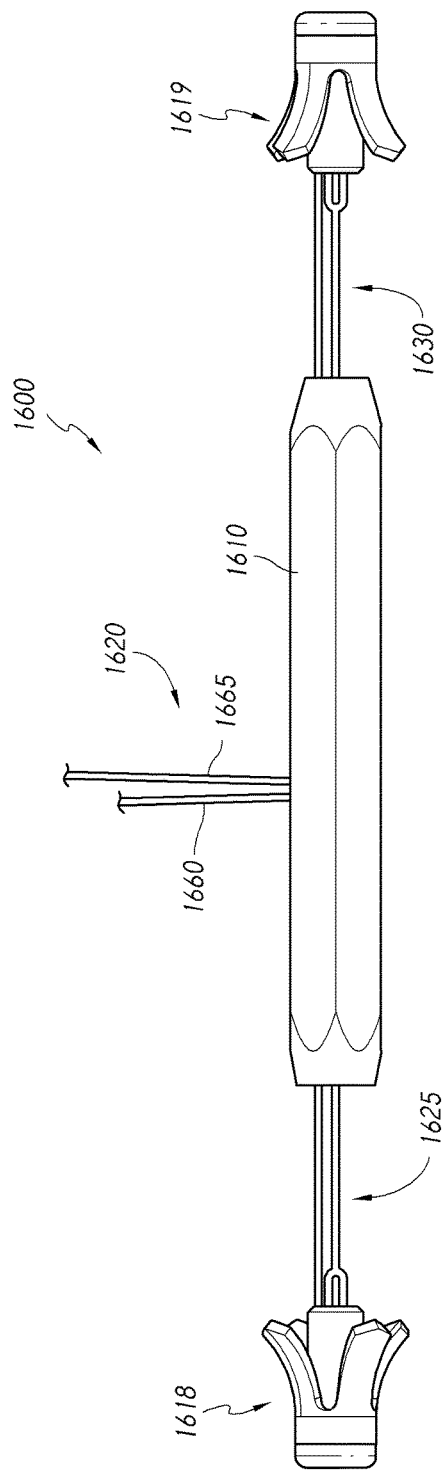

FIGS. 12A and 12B illustrate another embodiment of an implant 1600 that can be used in a joint arthrodesis or fusion procedure to treat hammer toe or another orthopedic deformity. According to some embodiments, the implant 1600 comprises an implant body 1610 (having a proximal end 1612 and a distal end 1615), a pair of bone anchors 1618, 1619, and a tension assembly 1620. In some embodiments, the tension assembly 1620 comprises a suture system or construct that includes one or more strands of suture. In some embodiments, the implant body 1610 comprises a longitudinal lumen 1622 that extends to openings along the proximal and distal ends 1612, 1615 of the implant body 1610. In addition, as with other implant embodiments described herein, the suture or other component of the tension assembly 1620 can extend into the internal lumen of the implant body 1610 through a side-hole or window 1623 positioned along a portion of the implant body 1610. In some embodiments, such a side-hole or window is located along or near the middle of the implant body (e.g., generally between the proximal and distal ends 1612, 1615 of the implant body). However, in other embodiments, the side-hole or window can be located closer to the proximal end 1612 or the distal end 1615 of the implant body 1610, as desired or required for a particular application or use.

With continued reference to FIG. 12A, the tension assembly 1620 can comprise a pair of opposed suture loops 1625, 1630, each of which is connected to one of the bone anchors 1618, 1619 (e.g., via eyelets or other securement members 1635, 1640). In addition, the tension assembly 1620 can comprise one or more locking or friction elements or portions 1650, 1655 formed in the suture construct of the tension assembly 1620, and a pair of suture tails or ends 1660, 1665. As discussed in greater detail herein (e.g., with reference to the embodiments of FIGS. 19 and 20), the locking or friction elements or portions 1650, 1655 of the suture system can include portions in which a suture strand is routed through a portion of itself (e.g., through a cannulated portion of the suture) over a particular distance or length. Friction or other resistive forces created between the suture strand routed through an interior portion of itself (e.g., via an opening in the suture sidewall) over the length of such elements or portions 1650, 1655 can help prevent or reduce the likelihood of relative movement of the adjacent portions of the suture. In such a knotless construct, the resulting friction or interference fit created within the suture loop at these locations helps maintain the position of the suture tails or ends 1660, 1665 that are routed through the side-hole or window 1623 to the exterior of the implant body 1610, even when the suture tails or ends are subjected to a certain level of tension (e.g., when the surgeon pulls the suture ends to create tension within the tension assembly). Thus, each of the locking elements 1650, 1655 can include a knotless construct, in which a section suture is routed through one sidewall of the tubular suture material and extends within the tubular suture material for a pre-defined distance before exiting the sidewall. Accordingly, upon application of tension to the suture system by a surgeon, the tension can be applied to and advantageously maintained between the opposing anchors of the implant.

Although the implant body 1610 illustrated herein is shown as generally straight, in other embodiments, the implant body 1610 may be formed with a bend having a desired angle or shape. In some embodiments, the angle can vary between 0 and 30 degrees (e.g., 0, 1, 2, 3, 4, 5, 6, 7, 8, 9, 10, 11, 12, 13, 14, 15, 16, 17, 19, 20, 21, 22, 23, 24, 25, 26, 27, 28, 29, 30 degrees, values between the foregoing angle ranges, etc.), greater than 30 degrees (e.g., 30-40, 40-50, 50-60 degrees, greater than 60 degrees, etc.), etc. In some embodiments, such a bend or angle in the implant body 1610 can approximate the natural angle of the phalangeal bones adjacent the targeted joint (e.g., the proximal and intermediate phalanges of a subject's foot, other phalangeal bones of a subject's foot or hand, etc.). Such a bend can help position the subject's toes, fingers or other bones in a more proper alignment and orientation following implantation of an implant. In some embodiments, the implant comprises two or more bends or angles. In other embodiments, the implant body comprises a non-linear shape along one or more portions. For example, one or more sections of the implant body can include a rounded or curved shape, a sinusoidal shape, an irregular shape and/or the like.

According to some embodiments, each tail or free end 1660, 1665 can be associated with a corresponding suture loop 1625, 1630. Thus, as discussed in greater detail herein, the surgeon can pull or otherwise manipulate the tails or free ends 1660, 1665 that extend to the exterior of the implant body 1610 to reduce or eliminate any slack in the corresponding suture loop 1625, 1630, and thus, provide a desired level of tension to the implant. For example, pulling of the tails or free ends can generate a tensile force between the two anchors 1618, 1619, resulting in compressing the adjacent bones in which the anchors are secured toward one another. Such a compressive force can help maintain contact between adjacent bone surfaces to facilitate in the arthrodesis or fusion process. Thus, applying tension to the suture tails 1660, 1665 allows the surgeon to selectively apply tension to the respective suture loops 1625, 1630, and thus, to the overall implant.

In other embodiments, the locking elements or portions 1650, 1655 of the suture loops include one or more other locking features, elements, designs or configurations (e.g., one-way knot constructs, separate components or devices that restrict relative movement between two adjacent portions of a suture strand, etc.). As discussed in greater detail herein, in the embodiment illustrated in FIG. 12A, the tension assembly 1620 can also be used as a repositioning element to adjust the axial or longitudinal position of the implant body 1610 during the implantation procedure. For example, once the implant body 1610 has been inserted within corresponding bores of proximal and distal bones (or proximal and distal portions of a bone, in a case of a fracture), the tension assembly 1620 can be used to move the implant body 1610 deeper into the proximal or distal bore, as desired or required. In some embodiments, for instance, a surgeon can manipulate the tails or free ends 1660, 1665 of the suture strands that pass through the side-hole or window 1623 of the implant body 1610 to accomplish the desired repositioning.

According to some embodiments, the implant body 1610 includes a rigid or semi-rigid structure having a hexagonal cross-sectional shape. In other embodiments, however, the implant body 1610 can include a different cross-sectional shape, such as, for example, circular, oval, square, rectangular, triangular, other polygonal, irregular and/or the like. In some embodiments, the use of an implant body 1110 having a polygonal shape helps ensure that the implant body will not rotate or otherwise move undesirably after completion of an implantation procedure. For example, the corners formed by the polygonal shape can provide for improved engagement with adjacent bone surfaces to reduce the likelihood of rotation or other movement when the implant is subject to various forces or moments post-implantation.

In some embodiments, the implant body 1610 comprises one or more biocompatible rigid, semi-rigid and/or flexible materials that provide the desired structural characteristics (e.g., strength, durability, flexibility, longevity, etc.) to the overall implant design. For example, in some embodiments, the implant body 1610 can include one or more polymeric materials (e.g., polyether ether ketone or PEEK, polyphenylene, polysulfone, polyethylene, etc.). In other embodiments, at least one or more of the components of the implant body 1610 comprise other materials, either in lieu of or in addition to suitable polymeric materials, that provide the desired properties to the anchor, such as, for example, metals or metal alloys (e.g., stainless steel, Nitinol or other shape memory materials, etc.), elastomeric materials (e.g., biocompatible rubbers) and/or the like. In some embodiments, the implant body comprises both a polymeric material (e.g., PEEK) and a metal or alloy (e.g., Nitinol, stainless steel, etc.).

According to some embodiments, the length of the implant body 1610 can be 5-50 mm (e.g., 5, 6, 7, 8, 9, 10, 11, 12, 13, 14, 15, 16, 17, 18, 19, 20, 21, 22, 23, 24, 25, 25-30, 30-35, 35-40, 40-45, 45-50 mm, lengths between the foregoing ranges, etc.). In other embodiments, the length of the implant body is less than about 5 mm (e.g., 0.5, 1, 1.5, 2, 2.5, 3, 3.5, 4, 4.5, 5 mm, lengths between the foregoing values, less than 0.5 mm, etc.). In one embodiment, an implant body 1610 used for repairing hammer toe in an adult subject is about 15 to 20 mm long (e.g., 15, 16, 17, 18, 19, 20 mm long).

In some embodiments, the outer cross-sectional dimension of the implant body 1610 can be 1-5 mm (e.g., 1, 1.5, 2, 2.5, 3, 3.5, 4, 4.5, 5 mm, dimensions between the foregoing values, etc.). In other arrangements, the outer cross-sectional dimension of the implant body 1610 is less than 1 mm (e.g., 0.1, 0.2, 0.3, 0.4, 0.5, 0.6, 0.7, 0.8, 0.9, 0.95, 1 mm, dimensions between the foregoing values, less than about 0.1 mm, etc.) or greater than 5 mm (e.g., 5-10, 10-15, 15-20 mm, greater than 20 mm, etc.), as desired or required by a particular application or use.

The proximal and distal bone anchors 1618, 1619 included in the implant of FIG. 12A can be similar or identical to those discussed herein with reference to other embodiments, such as, for example, the anchor 1230 incorporated into the implant design of FIG. 10 or the bone anchor 1390 illustrated in FIG. 11. In some embodiments, the anchors comprise one or more biocompatible rigid, semi-rigid and/or flexible materials that provide the desired structural characteristics (e.g., strength, durability, flexibility, longevity, etc.) to the overall implant design. For example, in some embodiments, the insert of the anchor and/or the anchor tube, including the deployable fingers or other engaging members extending therefrom, can include one or more polymeric materials (e.g., polyether ether ketone or PEEK, polyphenylene, polysulfone, polyethylene, etc.). In other embodiments, at least one or more of the components of the bone anchor comprise other materials, either in lieu of or in addition to suitable polymeric materials, that provide the desired properties to the anchor, such as, for example, metals or metal alloys (e.g., stainless steel, Nitinol or other shape memory materials, etc.), elastomeric materials (e.g., biocompatible rubbers) and/or the like. According to one embodiment, the insert of the anchor comprises PEEK and/or other polymeric materials, while the anchor tube comprises Nitinol, another shape memory material and/or another metal or alloy configured to at least partially radially expand (e.g., self-expand, with the assistance of a separate member, etc.) to engage adjacent bone tissue.

Additional details regarding the bone anchors illustrated herein are provided in U.S. Patent Publication No. 2013/0211451, filed as U.S. patent application Ser. No. 13/673,626 on Nov. 9, 2012 and published on Aug. 15, 2013, the entirety of which is incorporated by reference herein and explicitly made a part of this specification. In other embodiments, other bone anchor configurations can be employed into the implant design illustrated in FIG. 12A. The bone anchors can include any configuration suitable to permit the bone anchors to be inserted into a bone bore, and to thereafter engage the bone bore surface so as to resist being pulled from the bone bore in the direction opposite the insertion direction (e.g., in the direction of the implant body).

With continued reference to FIG. 12A, in some embodiments, the outer diameter or cross-sectional dimension of the bone anchors 1618 is identical or similar to the outer cross-sectional dimension of the adjacent implant body 1610. However, in other arrangements, the outer diameter or cross-sectional dimension of the bone anchors 1618 can be greater than or smaller than the outer cross-sectional dimension of the adjacent implant body 1610. For example, the outer diameter or cross-sectional dimension of the bone anchors 1618 can be about 0-20% (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 18-19, 9-20%, percentages between the foregoing, etc.) larger or smaller than the outer cross-sectional dimension of the adjacent implant body 1610, as desired or required.

The implant body 1610 and/or the bone anchors 1618, 1619 can be provided in a variety of sizes and shapes to accommodate for different indications, applications, subject and/or the like. Such implant bodies and/or anchors can be provided to the surgeon or other user in a kit. For example, a kit can include implant bodies 1610 of varying lengths and/or cross-sectional dimensions. In some embodiments, a kit includes bone anchors of different diameters or sizes, implants of varying cross-sectional dimensions and/or lengths and suture loops of varying designs, sizes, lengths and/or other properties. Thus, a surgeon or other practitioner can advantageously customize a procedure by combining various components. This can help provide for a more successful treatment procedure by using components that are best sized, shaped and/or otherwise configured for a specific application or use. In other embodiments, the implant body is configured be cut or otherwise reshaped in order to modify the implant for a particular use or application. Thus, is some embodiments, the implant body is provided in one or more lengths that can be shortened. In some embodiments, the implant body comprises materials and/or a configuration that is configured to be cut or otherwise shortened. For example, in some embodiments, the implant body can include segments that are scored, perforated, undermined and/or otherwise configured to be cut along certain predetermined locations.

According to some embodiments, the proximal bone anchor 1618 and the proximal end 1612 of the implant body 1610 can be inserted into a bore of a proximal bone (e.g., a proximal phalange) such that the distal end 1615 of the implant body extends distally from the proximal phalange by a desired first distance. In some embodiments, for example, the first distance is approximately 4 to 8 mm (e.g., 4, 5, 6, 7, 8 mm, distances between the foregoing values, etc.). Such a protruding distance beyond the proximal bone permits the distal bone to be safely and relatively easily placed over the protruding portion of the implant body. In some embodiments, the distal bone anchor 1619 can be seated in the bone bore of a distal bone (or distal bone portion), such as the intermediate phalange of a subject's foot. In such configurations, the tension assembly 1620 can include sufficient slack to allow the proximal bone anchor 1618 and the distal bone anchor 1619 to be separately seated in the respective bone bores while the proximal and intermediate phalanges are displaced from one another.

According to some embodiments, with reference to the implant of FIG. 12A, the distal bone (e.g., intermediate phalange) can then be positioned adjacent to the proximal bone (e.g., proximal phalange) such that the distal end 1615 of the implant body 1610 extends into the bone bore of the distal bone. Slack in the proximal suture loop 1630 can be taken up (e.g., reduced or eliminated) by applying tension to the corresponding suture tail or free end 1665. In some embodiments, in doing so, the interaction between the suture tail or free end 1665 and the inner surface of the side-hole or window 1623 can displace the implant body 1620 distally within the bone bores. In one embodiment, the position of the implant body 1620 within the bone bores may be adjusted until substantially equal lengths of the implant body 1610 are positioned within each of the phalanges (as can be visually confirmed when the side-hole 1623 is aligned with the joint between the phalanges). However, in other embodiments, it may be desirable to move the implant body deeper into the distal or proximal bore, such that the relative length of the implant body positioned in the distal and proximal bores is unequal. For example, in some embodiments a longer portion of the implant body (e.g., 50-60, 60-70, 70-80, 80-90% of the overall implant body length) is positioned within the distal bore or the proximal bore of the adjacent bones or bone portions along which fusion is sought, as desired or required. In one embodiment, the implant body 1610 is urged as deep as possible into the distal bore, such that a distal end of the implant body 1610 abuts and contacts the distal anchor 1619 positioned and secured within the distal bore.

With the implant body 1610 positioned as desired, one or more of the suture tails or free ends 1660, 1665 can be pulled so as to apply tension to the suture loops 1625, 1630, thus drawing the bone anchors 1618, 1619, and consequently, the proximal and intermediate phalanges toward one another. In doing so, the joint between the phalanges is placed in compression. As discussed in greater detail herein, the knotless locking or friction elements 1650, 1655 along each of the suture loops 1625, 1630 are configured to maintain this compression post-implantation. In some embodiments, at the end of an implantation procedure, the surgeon can optionally secure the suture free ends to each other (e.g., using one or more knots), trim such free ends and/or perform one or more other steps, ad desired or required.

According to some embodiments, once the implant body 1610 can be initially inserted within the proximal and distal bores and subsequently moved to a desired axial position (e.g., deeper into the distal bore, deeper into the proximal bore, etc., the side hole or window of the implant body may not be located at or near the targeted joint being treated. For example, the window 1623, and thus the suture tails or free ends that pass therethrough, can be located a particular distance (e.g., 0-10 mm, 0-1, 1-2, 2-3, 3-4, 4-5, 5-6,6-7, 7-8, 9, 10 mm, greater than 10 mm, distances between the foregoing values, etc.) distal or proximal to the joint or other bone interface. Thus, in some embodiments, once the implant body is moved either proximally or distally into a corresponding bone bore, the free end or tail of the suture system exiting the window can be routed along the outside of the implant body until it reached the joint. Thus, in some embodiments, the suture line or other elastomeric component comprising the suture loop and other portions of the suture system can comprises the necessary properties (e.g., strength, durability, flexibility, etc.) to transmit the tensile forces along the entire suture length, include any portion that is situation between the outside of the implant body and the inside diameter or portion of a corresponding bone bore.

In other embodiments, the distal (or proximal) bore can be created entirely through the targeted bone (e.g., phalange). Thus, the tension system in the implant of FIG. 12A (and/or any other implant disclosed herein) can be reconfigured to that the tails or free ends of a suture can be routed entirely through a bone to an opening opposite of the targeted joint being fused or otherwise treated. Thus, for example, for the implant of FIG. 12A, once the free ends or tails 1660, 1665 of the suture system 1620 exit the window 1623 of the implant body 1610, they can be routed distally or proximally (e.g., past the corresponding anchors 1619, 1618), along an area generally between the outside of the anchor and the insider diameter of the bone bore, toward a distal or proximal opening of the adjacent bones being fused.

Figure 12C:
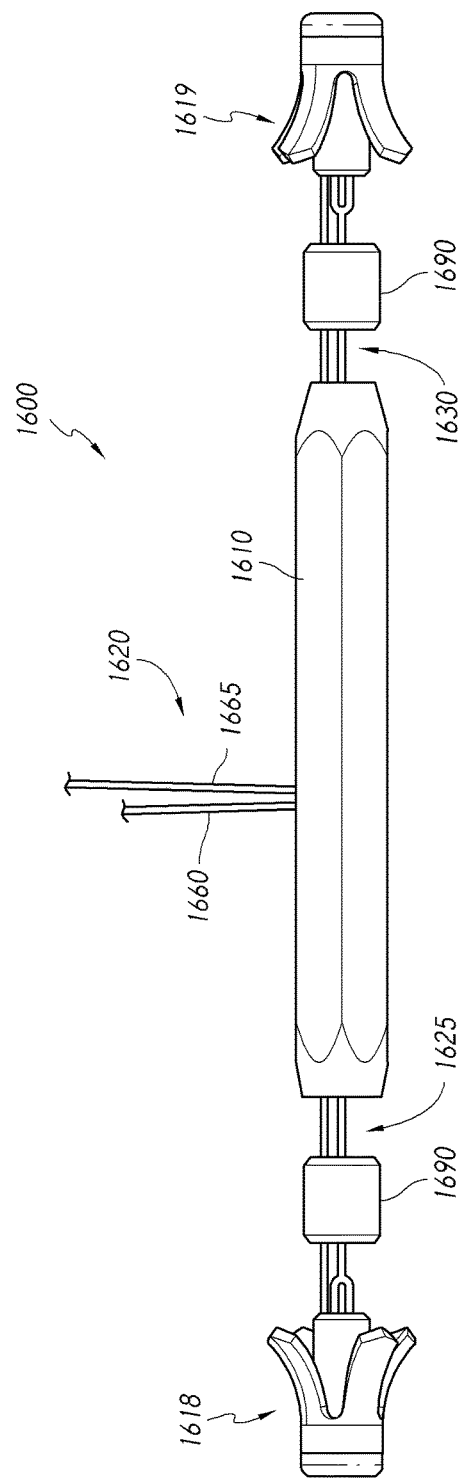
FIG. 12C illustrates an orthopedic repair implant according to another embodiment.

As shown in FIG. 12C, an elastomeric insert 1690 can be positioned on one or more sides of the implant body 1610 (e.g., between the implant body and the adjacent anchor or other bone engaging element). Such an insert or other component 1690 can include a spring (e.g., coil spring), another elastomeric, compressible or resilient sleeve, component or material (e.g., rubber insert) and/or the like. In some embodiments, such an insert 1690 can help increase or otherwise enhance the tension created within an implant once the tension system is manipulated. For example, in one embodiment, the insert 1690 is sized, shaped and otherwise configured so that, upon application of tension to the implant, the insert is squeezed or otherwise positioned between one end of the implant body and an adjacent anchor. Thus, as a result of such contact, the insert 1690 can be at least partially axially or longitudinally compressed to further increase the tension in the implant (e.g., and thus, increase the compressive forces maintained between adjacent bones being fused). Such an insert can be incorporated into any of the implant embodiments disclosed herein or variations thereof In some embodiments, as discussed herein, before an implant (e.g., the implant illustrated in FIGS. 12A and 12B) is positioned within a joint, certain preparatory steps can be performed to the adjacent bones of the joint. For example, the joint can be at least partially exposed or resected and the adjacent bone surfaces of the joint can undergo a particular rasping or other tissue removal step. For instance, a rasp or other bone cutting tool or method can be used to remove cartilage and/or bone tissue along each adjacent bone, resulting in bone to bone (e.g., bleeding bone to bleeding bone) contact. Further, before, during or after implantation of the implant into the joint, one or more graft or other materials or inserts can be positioned along the joint to promote fusion of the joint.

According to some embodiments, a proximal and/or distal portion of the implant body (e.g., along either side of a joint or other point of fusion) is configured to extend across two or more bones (e.g., phalanges). Thus, in some embodiments, an implant body is configured to span across three or more bones.

FIGS. 13-18 schematically illustrate sequential steps of a method of treating a foot joint deformity, such as, for example, hammer toe, using the implantable orthopedic repair implant 1000, according to one embodiment. During the arthrodesis procedure, portions of a pair of adjacent bones to selected to be fused that create the joint are resected and a bore hole is drilled into each the adjacent bones such that are substantially parallel and opposing. The drilled holes are large enough to accept the implant body 1110. Such an embodiment can be used with any configuration of an implant disclosed herein, including, without limitation, the implants depicted in FIGS. 2A, 10 and 12A.

Figure 13:
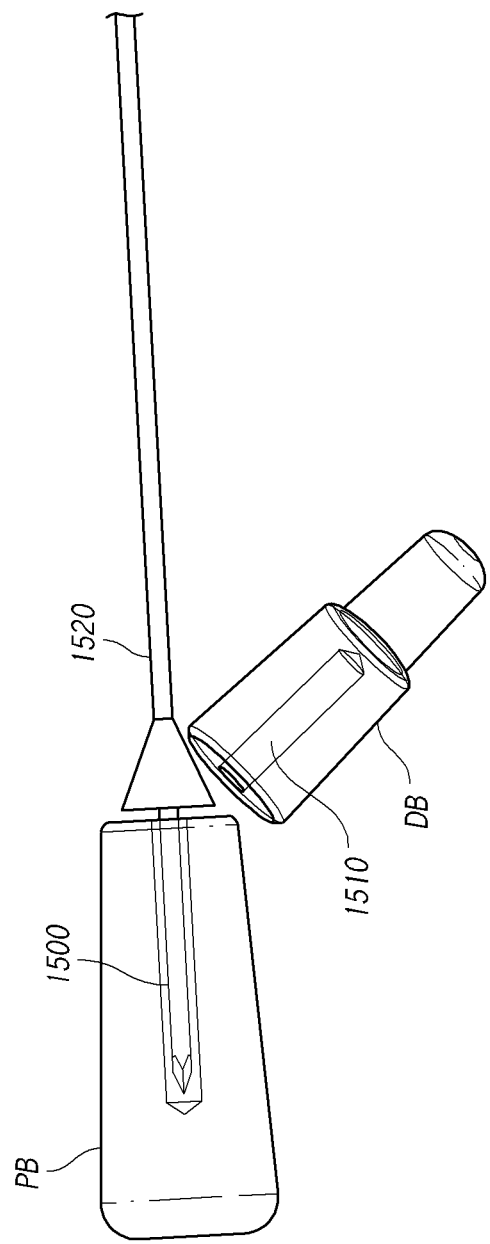
FIGS. 13-18 are schematic illustrations of sequential steps of a method of treating a foot joint deformity using an orthopedic repair implant according to one embodiment.

In the illustrated embodiment, as shown in FIG. 13, bone bores 1500, 1510 are formed, respectively, in the proximal and intermediate phalanges PB, DB after dissecting the soft tissues connecting the phalanges. In the illustrated embodiment, the bone bores 1500, 1510 can be formed using a bone drill, awl or similar device 1520. In some embodiments, the bone bores 1500, 1510 are drilled to a predetermined depth, as dictated by the implanting orthopedic specialist or as required by a particular procedure or protocol.

According to any of the implantations and fusion methods and procedures disclosed herein, preparation of the targeted bone surfaces (e.g., decertification, drilling, etc.) can be performed, at least in part, using the tools and other devices disclosed in U.S. Provisional Patent No. 61/887,132, filed Oct. 4, 2013 and titled CIRCULATING BONE RASP, the entirety of which is hereby incorporated by reference herein and made a part of this specification.

Figure 14:
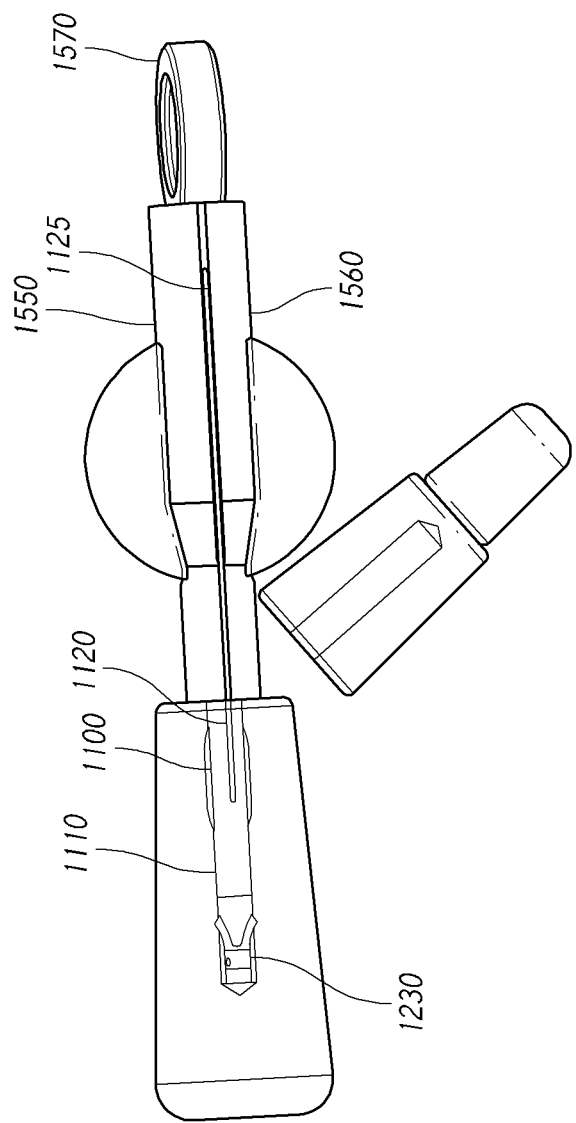

Next, as shown in FIG. 14, the implant 1000 can be partially inserted into the bone bore 1500 with the aid of a delivery tool 1550. In the illustrated embodiment, the delivery tool 1550 comprises a cannulated main body 1560 and a pull tab 1570. As shown, the distal end 1145 of the implant body 1110 can be received within the cannulated main body 1560, and the suture loop of the positioning element 1125 can be secured to the pull tab 1570. As further shown, in the configuration of FIG. 13, the bone anchor 1230 of the implant 1100 abuts the open proximal end 1140 of the implant body 1110. Although not illustrated in FIG. 13, in such a configuration, slack can exist in the tension assembly 1120 that is attached to the main body 1560 of the delivery tool 1550. Such slack can permit for the subsequent repositioning of the implant body 1110 as discussed in greater detail herein. As further shown in FIG. 13, the implant 1100 can be initially inserted fully into the bone bore 1500.

Figure 15:
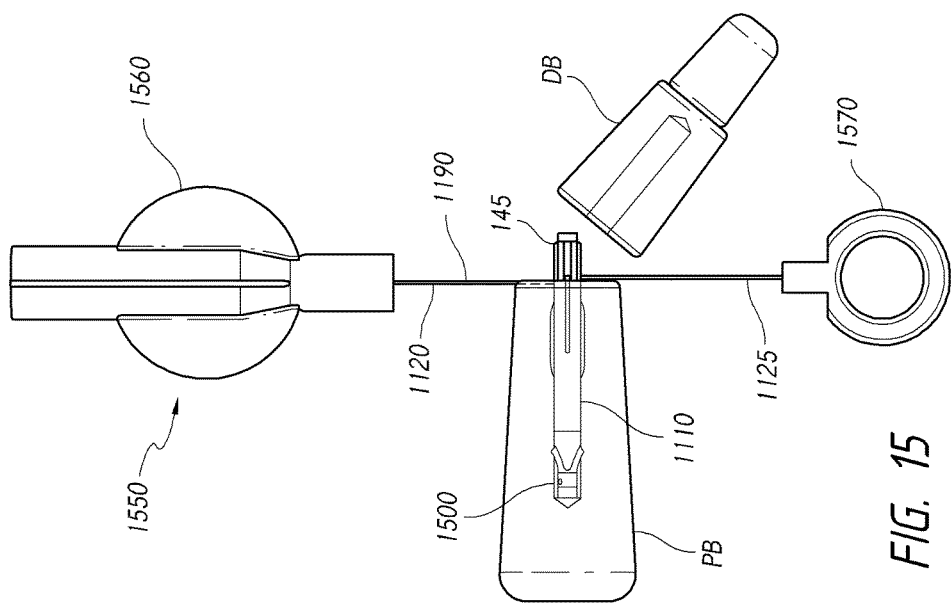

As shown in FIG. 15, according to some embodiments, the cannulated main body 1560 of the delivery tool 1550 can be removed from the distal end 1145 of the implant body 1110, and the pull tab 1570 can be separated from the cannulated main body 1560. As further shown in FIG. 15, the positioning element 1125 can be attached to the pull tab 1570, and the suture tail 1190 of the tension assembly 1120 can be attached to the cannulated main body 1560. Further, the distal end 1145 of the implant body 1110 can extend distally from the proximal bone PB (e.g., proximal phalange) by a pre-determined distance based on the length of the implant body 1110 and the insertion depth into the bone bore 1500. In various embodiments, such a distance is relatively small to facilitate ease of subsequent steps in the repair procedure. The distance can be selected to facilitate positioning the intermediate phalange proximate the interphalangeal joint to be repaired. In some embodiments, the procedure is performed, and the implant 1100 is configured, so that the distal end 1145 initially extends about 5 mm from the distal face of the proximal bone PB (e.g., proximal phalange) upon initial insertion of the implant body 1110 into the bone bore 1500. However, in other embodiments, such a distance can be greater or less than 5 mm (e.g., 1, 2, 3, 4, 5, 6, 7, 8, 9, 10 mm, greater than 10 mm, etc.).

Figure 16:
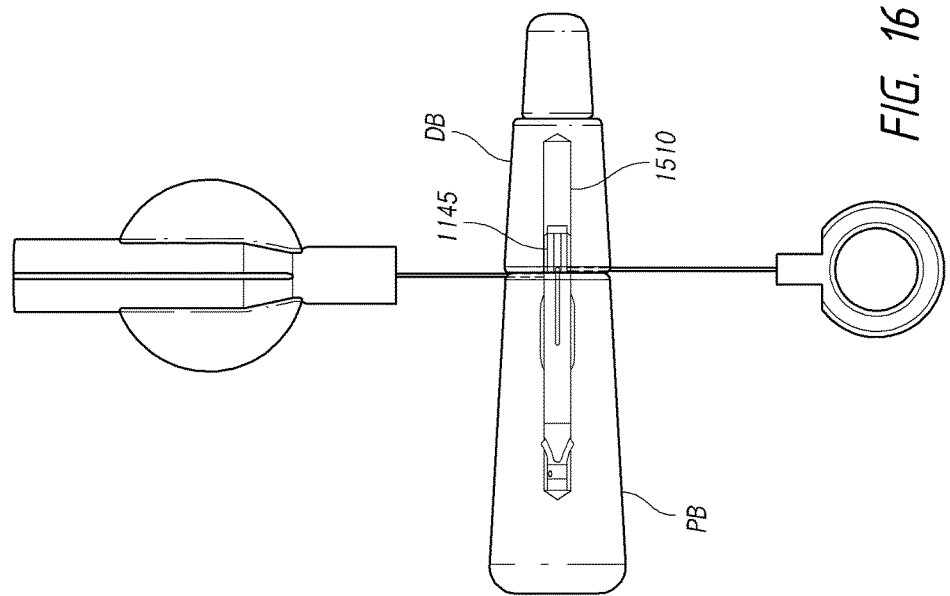
Figure 17:
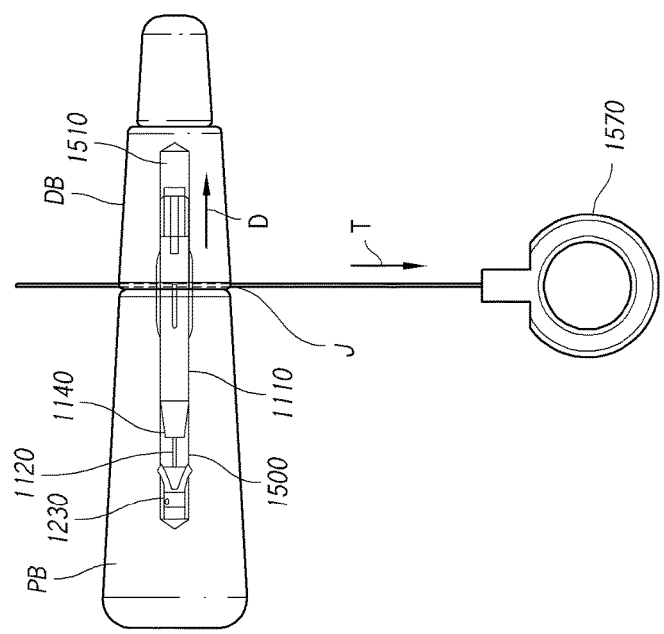

With reference to FIG. 16, the intermediate phalange DB can be positioned adjacent the proximal phalange PB, with the distal end 1145 of the implant body 1110 at least partially inserted into the bone bore 1510 of the intermediate phalange DB. As shown in FIG. 17, while holding the proximal and intermediate phalanges in place, the surgeon can apply tension to the pull tab 1570 (as indicated by the arrow T), which in turn causes the implant body 1110 to be displaced distally within the bone bores 1500, 1510 (as indicated by the arrow D). As can be seen in FIG. 17, the implant body 1110 can thus extend further into the bone bore 1110 than in the earlier phase of the repair method illustrated in FIG. 16. This can advantageously enhance the stability of the joint J upon completion of a fusion procedure.

In some embodiments, because the bone anchor 1230 has engaged the bone surfaces within the bone bore 1500, movement in the distal direction is generally resisted. Accordingly, displacement of the implant body 1110 can result in separation between the proximal end 1140 of the implant body 1110 and the bone anchor 1230, with slack in the tension assembly 1120 being partially or wholly taken up by such separation.

With reference to FIG. 18, applying tension to the main body 1560 (as indicated by the arrow P) can apply tension to the tension assembly 1120 between the bone anchor 1230 and the expandable element 1170 at the distal end 1145 of the implant body 1110. In some embodiments, since the bone anchor 1230 and the expandable element 1170 are positively engaged with bone surfaces within the respective bone bores 1500, 1510, tension applied to the tension assembly 1120 can cause the adjacent bones PB, DB (e.g., proximal and intermediate phalanges) to be drawn toward one another so as to place the joint J in compression (as indicated by the arrows C in FIG. 18). In various embodiments, the tension assembly 1120, and in particular, the sliding knot 1200, are configured to retain the tension assembly under tension, thus maintaining compression on the joint J post-implantation.

In some embodiments, the tension assembly 1120 and the positioning element 1125 are formed of separate suture structures. In other embodiments, however, these components may be combined, at least partially, into a single suture structure or construct that is operatively coupled to the bone anchor 1230 and the implant body 1110. Also, in various embodiments, the steps of applying tension to the positioning element 1125 and applying tension between the bone anchor 1230 and the expandable element 1170 can be performed as separate steps (as shown in FIGS. 17 and 18). Alternatively, such steps can be performed substantially concurrently by applying tension to a single suture tail of an appropriately constructed suture construct.

Figure 19:
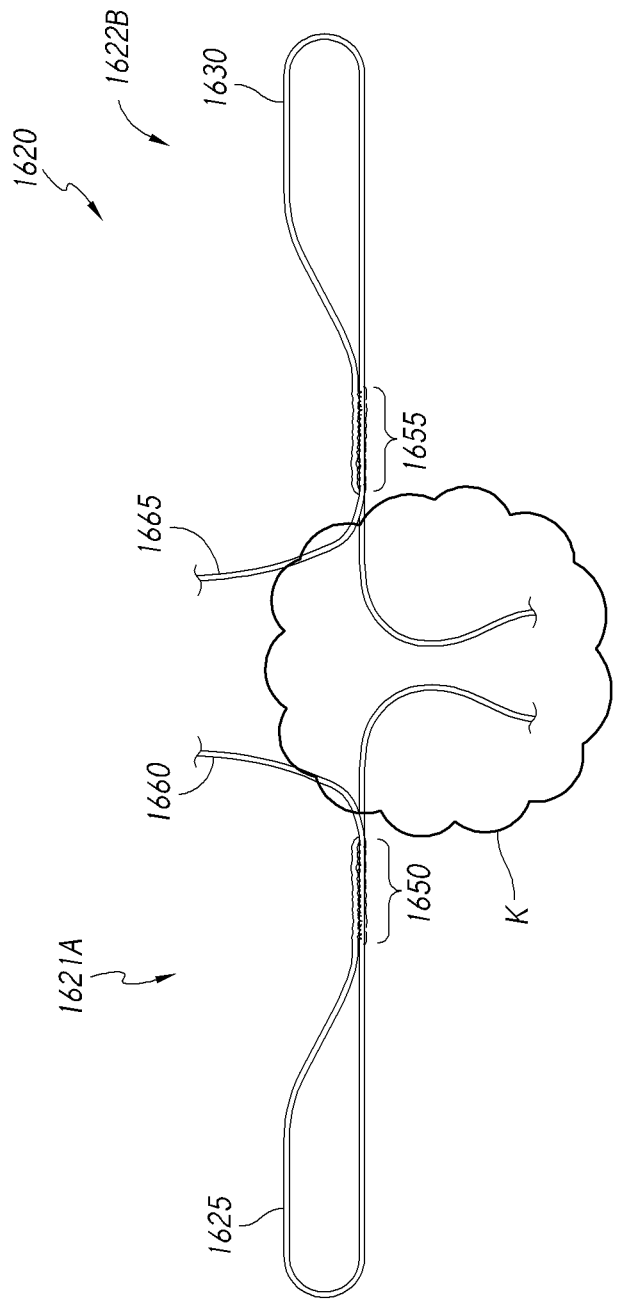
FIGS. 19 and 20 illustrate one embodiment of a knotless suture system configured for use in the implant depicted in FIG. 12A.
Figure 20:
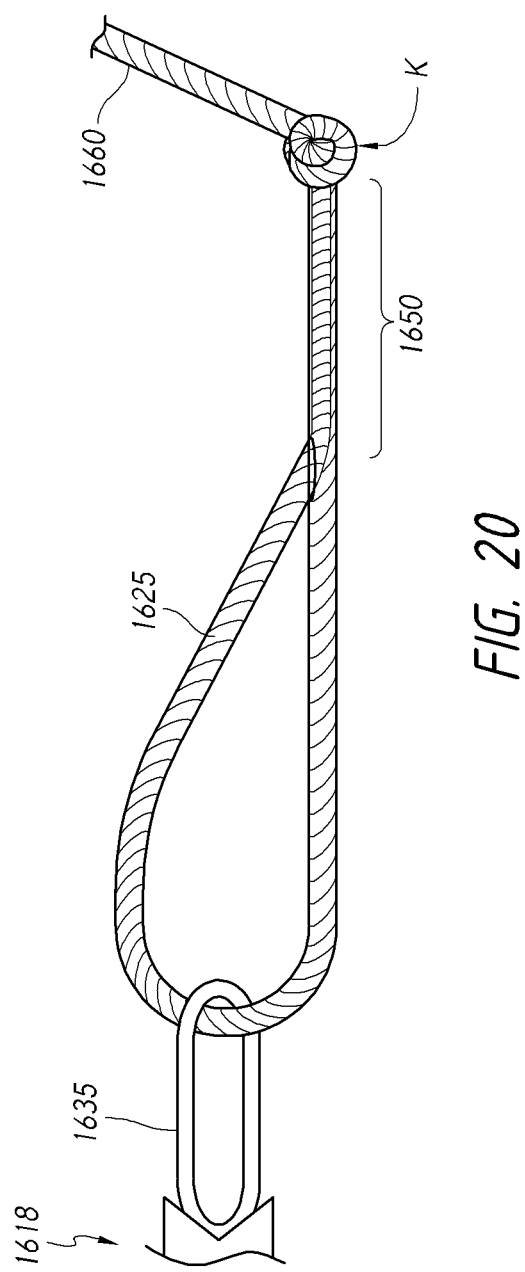

FIGS. 19 and 20 illustrate different views of one embodiment of a knotless suture system configured to be used in a tension assembly 1620 for any of the implant configurations disclosed herein. As shown, the suture system can include two separate suture strands 1621A, 1621B that can be secured to each other to form a knot K or other structure. As discussed herein with reference to several implant embodiments, such a knot K or other joining structure can be strategically positioned within an interior lumen of an implant body 1610. In some embodiments, the knot K can include an outer cross-sectional dimension that is greater than the size of side-hole or window of the implant body 1610, thereby securely maintaining the knot K and other portions of the tension system 1620 within an interior of the implant body 1610. In alternative embodiments, the tension system 1620 includes only a single strand of suture.

With continued reference to the illustrated embodiment, free ends or tails 1660, 1665 of suture loops 1625, 1630 can pass through a side-hole or window of the implant body and exit to the exterior of the implant body. In some embodiments, as discussed in greater detail above, a surgeon can manipulate (e.g. pull) these free ends or tails to provide tension to the implant and create compression in the joint targeted for fusion.

In some embodiments, as illustrated in the detailed schematic view of FIG. 20, the suture strand can loop around an eyelet or securement feature 1635 of a bone anchor or other bone engaging member and pass through an interior portion of itself during the return loop along a locking or friction element or portion 1650 of the loop. In some embodiments, the suture is cannulated to facilitate the passage of the suture through its interior along such a portion 1650. As noted herein, such a configuration helps create a knotless suture system that is capable of maintaining a threshold level of tension to the implant. For example, as the surgeon pulls on the free end or tail 1660, slack in suture loop 1625 is reduced or eliminated. With reference to FIG. 20, as the free end 1660 is pulled, a portion of the suture looping around the eyelet or other securement feature 1635 of the anchor 1618 passes through the interior of a section of the suture loop (e.g., along the locking or friction element or portion 1650). The frictional forces between the suture sections along this friction portion 1650 help prevent the suture loop from loosening and creating slack in the tension assembly. Accordingly, the tension created by manipulating the free ends or tails of the sutures can be advantageously maintained without a knot or additional securement feature or method.

According to some embodiments, any of the suture structures disclosed herein comprise surgical suture comprising one or more biocompatible polymeric materials, such as, for example, ultra-high-molecular-weight polyethylene, other types of polyethylene, other polymeric materials and/or the like. In some configurations, the suture includes one or more elastomeric materials (e.g., rubber bands or other rubber elastics or components) and/or other elastic materials or features. In one embodiment, the diameter of the suture is about 0.2 to 0.6 mm (e.g., 0.2, 0.25, 0.3, 0.35, 0.4, 0.45, 0.5, 0.55, 0.6 mm, diameter between the foregoing values, etc.). In other embodiments, however, the suture diameter can be greater than 0.6 mm or smaller than 0.2 mm, as desired or required. In other embodiments, however, the tension system can include an elastomeric component or member that is not a suture, but is nevertheless capable to providing the necessary tension to the implant and withstanding the necessary forces, moments and other elements to which it is subjected. Such an elastomeric component can include a flexible insert and/or the like.

In some embodiments, the locking or friction element or portion 1650 of a knotless suture system can be configured to withstand a maximum of 5 to 20 pounds of force before failing (e.g., 5, 6, 7, 8, 9, 10, 11, 12, 13, 14, 15, 16, 17, 18, 19, 20 pounds, values between the foregoing, etc.). In other arrangements, depending on the specific protocol, the maximum fail force can be lower than 5 pounds or greater than 20 pounds, as desired or required. In some embodiments, the end portions of the suture tails or free ends that are grasped or otherwise manipulated by the surgeon during a procedure can be configured to comprise a lower maximum force threshold (e.g., in some embodiments, about 1 to 30% lower failure threshold). Such portions can be limited to portions of the implant's tension assembly that are not routed through an implant body. Thus, if an upper force threshold is realized, the end portions of the suture tails or free ends (e.g., the portions with the lower force threshold) will fail and will be sacrificed to protect the remaining portions of the tension assembly (e.g., the suture loops, the friction portions, etc.).

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the invention is susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning a proximal or distal end of the implant body" include "instructing positioning a proximal or distal end of the implant body." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm" Terms or phrases preceded by a term such as "substantially" include the recited term or phrase. For example, "substantially parallel" includes "parallel."

What is claimed is:

1. An implant for correcting a deformity in or near a joint of a subject, comprising:
    an implant body comprising an internal lumen extending from a first end to a second end of the implant body, the implant body having a wall that defines the internal lumen, wherein the implant body is rigid;
    wherein the implant body comprises a suture side hole extending through the wall of the implant body, the suture side hole being positioned between the first and second ends of the implant body, and wherein the suture side hole provides access to the internal lumen from an exterior of the implant body; and
    a tension assembly comprising a first bone anchor and a second bone anchor, wherein the first and second bone anchors are positioned on opposite sides of the implant body;
    the tension assembly further comprising at least one adjustable suture loop coupling the first bone anchor to the second bone anchor, wherein at least a portion of the at least one adjustable suture loop is positioned within the internal lumen of the implant body;
    wherein the at least one adjustable suture loop comprises at least one suture tail that extends through the suture side hole and to an exterior of the implant body, wherein, upon deployment and fixation of the first and second bone anchors within bone bores of a subject and upon the application of tension to the at least one suture tail in a direction away from the implant body, a tension between the first and second bone anchors is increased.

2. The implant of claim 1, further comprising a positioning element located along the implant body, the positioning element being configured to facilitate adjustment of the implant body within corresponding bone bores of a subject once the implant has been located therein,
wherein the at least one adjustable suture loop comprises at least one knotless construct, the at least one knotless construct comprising a portion of the at least one adjustable suture loop routed through an interior of a section of the at least one adjustable suture loop;
wherein each of the first and second bone anchors comprises an eyelet, wherein a portion of the at least one adjustable suture loop traverses through the eyelets of the first and second bone anchors to secure the at least one adjustable suture loop to the first and second bone anchors;
wherein a cross-sectional shape of the implant body is polygonal; and
wherein the joint of the subject comprises a toe, and the deformity comprises hammer toe.

3. The implant of claim 1,
wherein the at least one adjustable suture loop comprises at least one knotless construct, the at least one knotless construct comprising a portion of the at least one adjustable suture loop routed through an interior of a section of the at least one adjustable suture loop; and
wherein each of the first and second bone anchors comprises a securement feature, wherein a portion of the at least one adjustable suture loop traverses through the securement features of the first and second bone anchors to secure the at least one adjustable suture loop to the first and second bone anchors.

4. The implant of claim 1, further comprising a sliding knot formed by the at least one adjustable suture loop, wherein the sliding knot is maintained within the interior lumen of the implant body.

5. The implant of claim 4, wherein an outer dimension of the sliding knot is greater than the suture side hole.

6. The implant of claim 1, wherein each of the first and second bone anchors comprises a plurality of deflectable fingers configured to engage bone at an implantation site.

7. The implant of claim 1, wherein the at least one adjustable suture loop comprises at least one knotless construct, wherein the at least one knotless construct comprises a portion of the at least one adjustable suture loop routed through an interior of a section of the at least one adjustable suture loop.

8. The implant of claim 1, wherein the implant body comprises a hexagonal or other polygonal cross-sectional shape.

9. The implant of claim 1, wherein the implant body comprises at least one bend or angle along a length of the implant body.

10. An implant for correcting a deformity in or near a joint of a subject, comprising:
an implant body comprising an internal lumen, wherein the implant body is rigid;
a first bone anchor and a second bone anchor, wherein the first and second bone anchors are configured to be placed on opposite sides of the implant body when the implant is assembled for use; and
at least one adjustable suture loop coupling the first bone anchor to the second bone anchor, wherein at least a portion of the at least one adjustable suture loop is positioned within the internal lumen of the implant body;
wherein the at least one adjustable suture loop comprises at least one suture tail that extends through a side hole of the implant body and to an exterior of the implant body, wherein the at least one adjustable suture loop is configured to maintain tension between the first and second bone anchors upon implantation.

11. The implant of claim 10, further comprising a sliding knot formed by the at least one adjustable suture loop, wherein the sliding knot is maintained within the interior lumen of the implant body.

12. The implant of claim 11, wherein an outer dimension of the sliding knot is greater than the side hole.

13. The implant of claim 10, wherein the at least one adjustable suture loop comprises at least one knotless construct, wherein the at least one knotless construct comprises a portion of the at least one adjustable suture loop routed through an interior of a section of the at least one adjustable suture loop.

14. The implant of claim 10, wherein the implant body comprises at least one bend or angle along a length of the implant body.

15. The implant of claim 10,
wherein the at least one adjustable suture loop comprises at least one knotless construct, the at least one knotless construct comprising a portion of the at least one adjustable suture loop routed through an interior of a section of the at least one adjustable suture loop; and
wherein each of the first and second bone anchors comprises an eyelet, wherein a portion of the at least one adjustable suture loop traverses through the eyelets of the first and second bone anchors to secure the at least one adjustable suture loop to the first and second bone anchors.

16. An implant for correcting a deformity in or near a joint of a subject, comprising:
an implant body comprising an internal lumen, wherein the implant body is rigid;
a first bone anchor and a second bone anchor, wherein the first and second bone anchors are configured to be placed on opposite sides of the implant body; and
at least one adjustable suture loop coupling the first bone anchor to the second bone anchor, wherein at least a portion of the at least one adjustable suture loop is configured to extend within the internal lumen of the implant body;
wherein the at least one adjustable suture loop comprises at least one tail that extends through a side opening of the implant body; and
wherein the at least one adjustable suture loop is configured to maintain tension between the first and second bone anchors upon implantation.

17. The implant of claim 16,
wherein the at least one adjustable suture loop comprises at least one knotless construct, the at least one knotless construct comprising a portion of the at least one adjustable suture loop routed through an interior of a section of the at least one adjustable suture loop; and
wherein each of the first and second bone anchors comprises an eyelet, wherein a portion of the at least one adjustable suture loop traverses through the eyelets of the first and second bone anchors to secure the at least one adjustable suture loop to the first and second bone anchors.

* * * * *